United States Patent
Hosaka et al.

(10) Patent No.: US 7,531,655 B2
(45) Date of Patent: May 12, 2009

(54) LARGE CONDUCTANCE CALCIUM-ACTIVATED K CHANNEL OPENER

(75) Inventors: Toshihiro Hosaka, Tokyo (JP); Mari Kusama, Saitama (JP); Kiyomi Ohba, Osaka (JP); Rikako Kono, Saitama (JP); Shuntarou Kohnomi, Toda (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 229 days.

(21) Appl. No.: 10/531,330

(22) PCT Filed: Oct. 15, 2003

(86) PCT No.: PCT/JP03/13194

§ 371 (c)(1),
(2), (4) Date: Apr. 14, 2005

(87) PCT Pub. No.: WO2004/035570

PCT Pub. Date: Apr. 29, 2004

(65) Prior Publication Data

US 2006/0135597 A1 Jun. 22, 2006

(30) Foreign Application Priority Data

Oct. 15, 2002 (JP) .............................. 2002-300860
Apr. 8, 2003 (JP) .............................. 2003-104260

(51) Int. Cl.
C07D 409/14 (2006.01)
(52) U.S. Cl. .................................. 544/333; 546/280.4
(58) Field of Classification Search .............. 546/280.4; 544/333
See application file for complete search history.

(56) References Cited

U.S. PATENT DOCUMENTS

| 3,743,656 A | 7/1973 | Brown et al. |
| 5,602,169 A | 2/1997 | Hewawasam et al. |
| 6,048,888 A | 4/2000 | Kawai et al. |

FOREIGN PATENT DOCUMENTS

| CA | 2247028 A1 | 5/2002 |
| EP | 0 842 923 A | 5/1998 |
| JP | 2000-351773 A | 12/2000 |
| WO | WO-96/40634 A | 12/1996 |
| WO | WO-98/04135 A | 2/1998 |
| WO | WO-02/34746 A2 | 5/2002 |
| WO | WO-02/83111 A | 10/2002 |

OTHER PUBLICATIONS

Katz et al., STN International, HCAPLUS Database, Columbus, OH, Accession No. 2002:115753, Reg. No. 83495-30-1 (2007).*
Irritable bowel syndrome: Tips on Controlling Your Symptoms [online], [retrieved on Jul. 6, 2006]. Retrieved from the Internet, URL; http://familydoctor.org/online/famdocen/home/common/digestive/disorders/112.html>.*
Diabetes Mellitus (DM) [online], [retrieved on Apr. 17, 2007]. Retrieved from the internet, URL; http://www.merck.com/mmpe/print/sec12/ch158b.html>.*
Chemical Abstracts, vol. 134, No. 3, Jan. 15, 2001.

* cited by examiner

*Primary Examiner*—Rebecca L Anderson
*Assistant Examiner*—Shawquia Young
(74) *Attorney, Agent, or Firm*—Birch, Stewart, Kolasch & Birch, LLP

(57) ABSTRACT

There are disclosed a large conductance calcium-activated K channel opener comprising a compound of the formula (I):

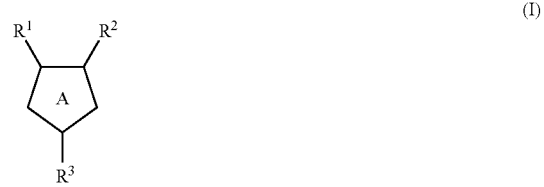

wherein ring A is a 5-membered heterocyclic ring containing any one of O, N or S, which ring may be substituted by $R^4$,
$R^1$ is aryl, heterocyclic or heterocycle-substituted carbonyl; $R^2$ is hydrogen, halogen, carboxy, amino, alkyl, alkoxycarbonyl, alkenyl or cycloalkyl; $R^3$ is aryl, heterocyclic or alkyl; and $R^4$ is hydrogen or alkyl, each of substituents may be substituted,
or a pharmaceutically acceptable salt thereof as an active ingredient.

9 Claims, No Drawings

LARGE CONDUCTANCE CALCIUM-ACTIVATED K CHANNEL OPENER

FIELD OF THE INVENTION

This invention relates to an excellent large conductance calcium-activated K channel opener containing a 5-membered heterocyclic compound as an active ingredient, which is useful for treatment of disorders or diseases such as pollakiuria, urinary incontinence, cerebral infarction, subarachnoid hemorrhage, and the like.

BACKGROUND OF THE INVENTION

Potassium is the most abundant intracelluar cation, and is very important in maintaining physiological homeostasis. Potassium channels are present in almost all vertebrate cells, and the potassium influx through these channels is indispensable for maintaining hyperpolarized resting membrane potential.

Large conductance calcium activated potassium channels (also BK channels or maxi-K channels) are expressed especially in neurons and smooth muscle cells. Because both of the increase of intracellular calcium concentration and membrane depolarization can activate maxi-K channels, maxi-K channels have been thought to play a pivotal role in regulating voltage-dependent calcium influx. Increase in the intracellular calcium concentration mediates many processes such as release of neurotransmitters, contraction of smooth muscles, cell growth and death, and the like. Actually, the opening of maxi-K channels causes strong membrane hyperpolarization, and inhibits these calcium-induced responses thereby. Accordingly, by inhibiting various depolarization-mediated physiological responses, a substance having an activity of opening maxi-K channels is expected to have potential for the treatment of diseases such as cerebral infarction, subarachnoid hemorrhage, pollakiuria, urinary incontinence, and the like.

There have been various reports on a large conductance calcium-activated potassium channel opener. For example, in International Publications WO96/40634 and WO99/36069, pyrrole derivatives have been disclosed, in Japanese Provisional Patent Publication No. 2000-351773, a furan derivative has been disclosed and in International Publication WO98/04135, a nitrogen-containing 5-membered derivative in which the nitrogen is substituted by phenyl group or benzyl group has been disclosed.

SUMMARY OF THE INVENTION

An object of the present invention is to provide an excellent large conductance calcium-activated K channel opener containing a 5-membered heterocyclic compound as an active ingredient, which is useful for treatment of disorders or diseases such as pollakiuria, urinary incontinence, cerebral infarction, subarachnoid hemorrhage, and the like.

The present inventors have studied intensively to solve the problems, and as a result, they have found that a certain kind of a 5-membered heterocyclic compound has an excellent large conductance calcium-activated K channel opening activity, whereby they have accomplished the present invention.

That is, the present invention is as mentioned below.

[1] A large conductance calcium-activated K channel opener comprising a 5-membered heterocyclic compound of the formula (I):

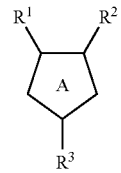

wherein ring A is a ring represented by any one of the formulae:

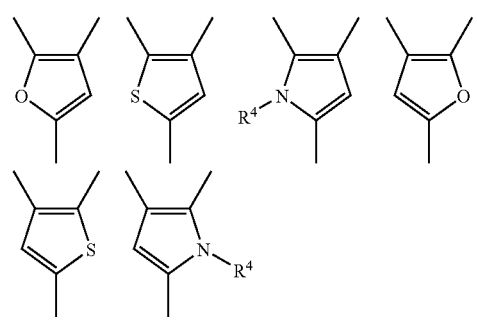

$R^1$ is a substituted or unsubstituted aryl, a substituted or unsubstituted heterocycle or a substituted or unsubstituted heterocycle-substituted carbonyl;

$R^2$ is hydrogen, a halogen, carboxy, a substituted or unsubstituted amino, a substituted or unsubstituted alkyl, an alkoxycarbonyl, a substituted or unsubstituted alkenyl or a cycloalkyl; $R^3$ is a substituted or unsubstituted aryl, a substituted or unsubstituted heterocycle or a substituted or unsubstituted alkyl; and $R^4$ is hydrogen or a substituted or unsubstituted alkyl, or a pharmaceutically acceptable salt thereof as an active ingredient.

[2] The large conductance calcium-activated K channel opener according to the above [1], wherein $R^1$ is (1) an aryl which may be substituted by a substituent(s) selected from the group consisting of nitro, amino, hydroxy, carbamoyl, cyano, carboxy, trifluoromethyl, alkoxycarbonyl, halogen, alkyl, hydroxyalkyl, alkoxy, alkoxyalkoxy, mono- or di-alkylamino, mono- or di-alkanoylamino, alkylthio, alkylsulfonyl, alkylsulfinyl, sulfamoyl, mono- or di-alkylsulfamoyl, alkylsulfonylamino and phenylalkoxy, (2) a heterocycle which may be substituted by a substituent(s) selected from the group consisting of nitro, hydroxy, formyl, carbamoyl, cyano, amino, carboxy, alkoxycarbonyl, halogen, alkyl, hydroxyalkyl, alkoxy, mono- or di-alkylamino, mono- or di-alkanoylamino, alkylthio, alkylsulfonyl, alkylsulfinyl, sulfamoyl and mono- or di-alkylsulfamoyl, or (3) a heterocycle-substituted carbonyl which may be substituted by a substituent(s) selected from the group consisting of nitro, hydroxy, carbamoyl, cyano, carboxy, alkoxycarbonyl, halogen, alkyl, hydroxyalkyl, alkoxy, alkanoyl, mono- or di-alkylamino, mono- or di-alkanoylamino, alkylthio, alkylsulfonyl, alkylsulfinyl, sulfamoyl and mono- or di-alkylsulfamoyl;

$R^2$ is (1) hydrogen, (2) halogen, (3) carboxy, (4) amino which may be substituted by a substituent(s) selected from the group consisting of formyl, alkyl, alkanoyl, alkylsulfonyl and alkoxycarbonyl, (5) an alkyl which may be substituted by a substituent(s) selected from the group consisting of halogen, hydroxy, cyano, carboxy, carbamoyl, amino, aminosulfonyl, amidinothio, mono- or di-alkylamino, alkanoylamino, alkylsulfonylamino, hydroxyamino, mono- or di-alkylcarbamoyl, trifluoromethyl, alkoxy, alkylthio, alkylsulfinyl, alkylsulfonyl, alkylsulfonylamino, hydroxycarbamoyl, hydroxycarbamoyl which is substituted by one or two alkyl (s), alkylsulfonylcarbamoyl, sulfamoyl, mono- or di-alkylsulfamoyl, alkoxycarbonyl, heterocycle, heterocycle-substituted carbamoyl, heterocycle-substituted alkylcarbamoyl and heterocycle-substituted sulfonylcarbamoyl, (6) alkoxycarbonyl, (7) alkenyl which may be substituted by carboxy or alkoxycarbonyl, or (8) cycloalkyl;

$R^3$ is (1) an aryl which may be substituted by a substituent (s) selected from the group consisting of cyano, nitro, amino, halogen, trifluoromethyl, carboxy, hydroxy, carbamoyl, mono- or di-alkylamino, aminoalkyl, mono- or di-alkylaminoalkyl, mono- or di-alkylcarbamoyl, alkyl, hydroxyalkyl, alkzoxy, alkoxycarbonyl, alkanoyl, alkanoyloxy, alkanoyloxyalkyl, sulfo, alkylthio, alkylthioalkyl, alkylsulfonyl, sulfamoyl, mono- or di-alkylsulfamoyl and alkylsulfinyl, (2) a heterocycle which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (3) an alkyl which may be substituted by a substituent(s) selected from the group consisting of hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle; and $R^4$ is (1) hydrogen or (2) an alkyl which may be substituted by mono- or di-alkylammo.

[3] The large conductance calcium-activated K channel opener according to the above [1] or [2], wherein $R^1$ is a substituted or unsubstituted aryl or a substituted or unsubstituted heterocycle;

$R^2$ is carboxy, a substituted or unsubstituted amino, a substituted or unsubstituted alkyl, alkoxycarbonyl or a substituted or unsubstituted alkenyl; and $R^3$ is a substituted or unsubstituted aryl or a substituted or unsubstituted heterocycle.

[4] The large conductance calcium-activated K channel opener according to the above [1], wherein $R^1$ is (1) aryl which may be substituted by one or two halogen(s) or (2) a heterocycle which may be substituted by halogen or alkyl;

$R^2$ is alkyl which may be substituted by a substituent(s) selected from the group consisting of carboxy, carbamoyl, mono- or di-alkylcarbamoyl, hydroxycarbamoyl, hydroxycarbamoyl which is substituted by one or two alkyl(s), alkoxycarbonyl, alkylsulfonylcarbamoyl and heterocycle;

$R^3$ is (1) a heterocycle which may be substituted by one or two substituent(s) selected from the group consisting of amino, halogen, alkyl, alkoxy, mono- or di-alkylamino and alkylthio or (2) aryl which may be substituted by a substituent (s) selected from the group consisting of amino, halogen, alkyl, alkylthio, alkoxy and mono- or di-alkylamino; and $R^4$ is hydrogen or alkyl.

[5] The large conductance calcium-activated K channel opener according to the above [1], wherein $R^1$ is (1) aryl which may be substituted by one or two halogen(s), (2) thienyl which may be substituted by halogen or (3) pyridyl which may be substituted by alkyl;

$R^2$ is (1) carboxyalkyl, (2) carbamoylalkyl, (3) mono- or di-alkylcarbamoylalkyl, (4) alkoxycarbonylalkyl, (5) alkylsulfonylcarbamoylalkyl or (6) tetrazolylalkyl;

$R^3$ is (1) benzothienyl which may be substituted by halogen, (2) phenyl which may be substituted by a substituent(s) selected from the group consisting of halogen, alkylthio, alkyl, alkoxy and dialkylamino, (3) pyridyl which may be substituted by a substituent(s) selected from the group consisting of alkyl, alkoxy and dialkylamino, (4) pyrimidinyl which may be substituted by alkoxy, alkyl, dialkylamino or alkylthio, (5) thienyl which may be substituted by one or two alkyl(s), (6) thieno[3,2-b]pyridyl, (7) benzofuryl, (8) dihydrobenzofuryl or (9) indolyl which may be substituted by alkyl; and $R^4$ is hydrogen or alkyl.

[6] The large conductance calcium-activated K channel opener according to the above [1], wherein $R^1$ is (1) aryl which may be substituted by one or two halogen(s) or (2) thienyl which may be substituted by halogen;

$R^2$ is (1) carboxyalkyl, (2) carbamoylalkyl, (3) mono- or di-alkylcarbamoylalkyl, or (4) alkoxycarbonylalkyl;

$R^3$ is (1) benzothienyl which may be substituted by halogen, (2) phenyl which may be substituted by a substituent(s) selected from the group consisting of halogen, alkylthio, alkyl, alkoxy and dialkylamino, (3) pyridyl which may be substituted by a substituent(s) selected from the group consisting of alkyl, alkoxy and dialkylamino, (4) pyrimidinyl which may be substituted by alkoxy or dialkylamino, (5) thienyl which may be substituted by one or two alkyl(s), (6) thieno[3,2-b]pyridyl, (7) benzofuryl, (8) dihydrobenzofuryl or (9) indolyl which may be substituted by alkyl; and $R^4$ is hydrogen or alkyl.

[7] The large conductance calcium-activated K channel opener according to the above [1], wherein $R^1$ is (1) aryl which may be substituted by one or two halogen(s) or (2) thienyl which may be substituted by halogen;

$R^2$ is (1) carboxyalkyl or (2) alkoxycarbonylalkyl;

$R^3$ is (1) benzothienyl which may be substituted by halogen, (2) phenyl which may be substituted by a substituent(s) selected from the group consisting of halogen, alkylthio, alkoxy and dialkylamino, (3) pyridyl which may be substituted by alkoxy or dialkylamino, (4) pyrimidinyl which may be substituted by dialkylamino, (5) thienyl which may be substituted by one or two alkyl(s), (6) thieno[3,2-b]pyridyl or (7) indolyl which may be substituted by alkyl; and $R^4$ is hydrogen or alkyl.

[8] The large conductance calcium-activated K channel opener according to any one of the above [1] to [6], wherein $R^2$ is carboxymethyl or alkoxycarbonylmethyl.

[9] The large conductance calcium-activated K channel opener according to any one of the above [1] to [8], wherein the Ring A is a ring represented by either one of the formulae:

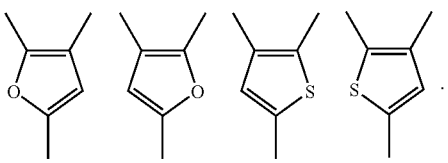

[10] A 5-membered heterocyclic compound of the formula (II):

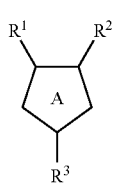

(II)

wherein ring A is a ring represented by any one of the formulae:

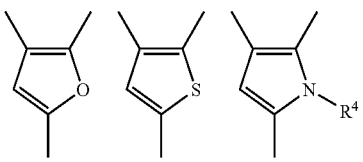

R$^1$ is a substituted or unsubstituted aryl, a substituted or unsubstituted heterocycle or a substituted or unsubstituted heterocycle-substituted carbonyl;
R$^2$ is a substituted alkyl;
R$^3$ is a substituted or unsubstituted aryl, a substituted or unsubstituted heterocycle or a substituted or unsubstituted alkyl; and
R$^4$ is hydrogen or a substituted or unsubstituted alkyl;
provided that when R$^1$ and R$^3$ are phenyl, R$^2$ is not carboxymethyl or ethoxycarbonylmethyl, or a pharmaceutically acceptable salt thereof.

[11] The 5-membered heterocyclic compound or a pharmaceutically acceptable salt thereof according to the above [10], wherein R$^1$ is a substituted or unsubstituted heterocycle, a substituted or unsubstituted heterocycle-substituted carbonyl, or an aryl substituted by two halogens.

[12] The 5-membered heterocyclic compound or a pharmaceutically acceptable salt thereof according to the above [10] or [11], wherein R$^1$ is (1) an aryl which may be substituted by a substituent(s) selected from the group consisting of nitro, amino, hydroxy, carbamoyl, cyano, carboxy, trifluoromethyl, alkoxycarbonyl, halogen, alkyl, hydroxyalkyl, alkoxy, alkoxyalkoxy, mono- or di-alkylamino, mono- or di-alkanoylamino, alkylthio, alkylsulfonyl, alkylsulfinyl, sulfamoyl, mono- or di-alkylsulfamoyl, alkylsulfonylamino and phenylalkoxy, (2) a heterocycle which may be substituted by a substituent(s) selected from the group consisting of nitro, hydroxy, formyl, carbamoyl, cyano, amino, carboxy, alkoxycarbonyl, halogen, alkyl, hydroxyalkyl, alkoxy, mono- or di-alkylamino, mono- or di-alkanoylamino, alkylthio, alkylsulfonyl, alkylsulfinyl, sulfamoyl and mono- or di-alkylsulfamoyl, or (3) a heterocycle-substituted carbonyl which may be substituted by a substituent(s) selected from the group consisting of nitro, hydroxy, carbamoyl, cyano, carboxy, alkoxycarbonyl, halogen, alkyl, hydroxyalkyl, alkoxy, alkanoyl, mono- or di-alkylamino, mono- or di-alkanoylamino, alkylthio, alkylsulfonyl, alkylsulfinyl, sulfamoyl and mono- or di-alkylsulfamoyl;

R$^2$ is an alkyl which may be substituted by a substituent(s) selected from the group consisting of halogen, hydroxy, cyano, carboxy, carbamoyl, amino, aminosulfonyl, amidinothio, mono- or di-alkylamino, alkanoylamino, alkylsulfonylamino, hydroxyamino, mono- or di-alkylcarbamoyl, trifluoromethyl, alkoxy, alkylthio, alkylsulfinyl, alkylsulfonyl, alkylsulfonylamino, hydroxycarbamoyl, hydroxycarbamoyl which is substituted by one or two alkyl(s), alkylsulfonylcarbamoyl, sulfamoyl, mono- or di-alkylsulfamoyl, alkoxycarbonyl, heterocycle, heterocycle-substituted carbamoyl, heterocycle-substituted alkylcarbamoyl and heterocycle-substituted sulfonylcarbamoyl;

R$^3$ is (1) an aryl which may be substituted by a substituent(s) selected from the group consisting of cyano, nitro, amino, halogen, trifluoromethyl, carboxy, hydroxy, carbamoyl, mono- or di-alkylamino, aminoalkyl, mono- or di-alkylaminoalkyl, mono- or di-alkylcarbamoyl, alkyl, hydroxyalkyl, alkoxy, alkoxycarbonyl, alkanoyl, alkanoyloxy, alkanoyloxyalky, sulfo, alkylthio, alkylthioalkyl, alkylsulfonyl, sulfamoyl, mono- or di-alkylsulfamoyl and alkylsulfinyl, (2) a heterocycle which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (3) an alkyl which may be substituted by a substituent(s) selected from the group consisting of hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle; and R$^4$ is (1) hydrogen or (2) an alkyl which may be substituted by mono- or di-alkylamino.

[13] The 5-membered heterocyclic compound or a pharmaceutically acceptable salt thereof according to the above [10] or [11], wherein R$^1$ is (1) an aryl which may be substituted by one or two halogen(s), or (2) a heterocycle which may be substituted by halogen or alkyl;

R$^2$ is an alkyl which may be substituted by a substituent(s) selected from the group consisting of carboxy, carbamoyl, mono- or di-alkylcarbamoyl, hydroxycarbamoyl, hydroxycarbamoyl which is substituted by one or two alkyl(s), alkoxycarbonyl, alkylsulfonylcarbamoyl and heterocycle; and R$^3$ is (1) a heterocycle which may be substituted by one or two substituent(s) selected from the group consisting of amino, halogen, alkyl, alkoxy, mono- or di-alkylamino and alkylthio, or (2) an aryl which may be substituted by a substituent(s) selected from the group consisting of amino, halogen, alkyl, alkylthio, alkoxy and mono- or di-alkylamino; and R$^4$ is hydrogen or alkyl.

[14] A 5-membered heterocyclic compound of the formula (III):

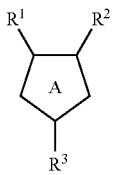

(III)

wherein ring A is a ring represented by any one of the formulae:

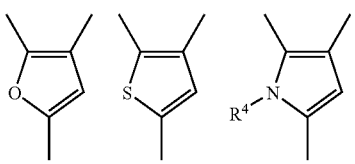

R¹ is a substituted or unsubstituted thienyl, or an aryl substituted by two halogens;
R² is substituted alkyl;
R³ is a substituted or unsubstituted aryl, a substituted or unsubstituted heterocycle or a substituted or unsubstituted alkyl; and
R⁴ is hydrogen or a substituted or unsubstituted alkyl; provided that when R¹ is 2-thienyl, R³ is not 2-thienyl;

or a pharmaceutically acceptable salt thereof.

[15] The 5-membered heterocyclic compound or a pharmaceutically acceptable salt thereof according to the above [14],
wherein R² is an alkyl which may be substituted by a substituent(s) selected from the group consisting of halogen, hydroxy, cyano, carboxy, carbamoyl, amino, aminosulfonyl, amidinothio, mono- or di-alkylamino, alkanoylamino, alkylsulfonylamino, hydroxyamino, mono- or di-alkylcarbamoyl, trifluoromethyl, alkoxy, alkylthio, alkylsulfinyl, alkylsulfonyl, alkylsulfonylamino, hydroxycarbamoyl, hydroxycarbamoyl which is substituted by one or two alkyl(s), alkylsulfonylcarbamoyl, sulfamoyl, mono- or di-alkylsulfamoyl, alkoxycarbonyl, heterocycle, heterocycle-substituted carbamoyl, heterocycle-substituted alkylcarbamoyl and heterocycle-substituted sulfonylcarbamoyl;
R³ is (1) an aryl which may be substituted by a substituent(s) selected from the group consisting of cyano, nitro, amino, halogen, trifluoromethyl, carboxy, hydroxy, carbamoyl, mono- or di-alkylamino, aminoalkyl, mono- or di-alkylaminoalkyl, mono- or di-alkylcarbamoyl, alkyl, hydroxyalkyl, alkoxy, alkoxycarbonyl, alkanoyl, alkanoyloxy, alkanoyloxyalkyl, sulfo, alkylthio, alkylthioalkyl, alkylsulfonyl, sulfamoyl, mono- or di-alkylsulfamoyl and alkylsulfinyl, (2) a heterocycle which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (3) an alkyl which may be substituted by a substituent(s) selected from the group consisting of hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle; and
R⁴ is (1) hydrogen or (2) an alkyl which may be substituted by mono- or di-alkylamino.

[16] The 5-membered heterocyclic compound or a pharmaceutically acceptable salt thereof according to the above [14],
wherein R² is an alkyl which may be substituted by a substituent(s) selected from the group consisting of carboxy, carbamoyl, mono- or di-alkylcarbamoyl, hydroxycarbamoyl, hydroxycarbamoyl which is substituted by one or two alkyl(s), alkoxycarbonyl, alkylsulfonylcarbamoyl and heterocycle;
R³ is (1) a heterocycle which may be substituted by one or two substituent(s) selected from the group consisting of amino, halogen, alkyl, alkoxy, mono- or di-alkylamino and alkylthio, or (2) an aryl which may be substituted by a substituent(s) selected from the group consisting of amino, halogen, alkyl, alkylthio, alkoxy and mono- or di-alkylamino; and
R⁴ is hydrogen or alkyl.

[17] The 5-membered heterocyclic compound or a pharmaceutically acceptable salt thereof according to the above [10] or [14],
wherein R¹ is thienyl which may be substituted by halogen (s);
R² is (1) carboxyalkyl, (2) carbamoylalkyl, (3) mono- or di-alkylcarbamoylalkyl, (4) alkoxycarbonylalkyl, (5) alkylsulfonylcarbamoylalkyl or (6) tetrazolylalkyl;
R³ is (1) benzothienyl which may be substituted by halogen, (2) phenyl which may be substituted by a substituent(s) selected from the group consisting of halogen, alkylthio, alkyl, alkoxy and dialkylamino, (3) pyridyl which may be substituted by a substituent(s) selected from the group consisting of alkyl, alkoxy and dialkylamino, (4) pyrimidinyl which may be substituted by alkoxy, alkyl, dialkylamino or alkylthio, (5) thienyl which may be substituted by one or two alkyl(s), (6) thieno[3,2-b]pyridyl, (7) benzofuryl, (8) dihydrobenzofuryl or (9) indolyl which may be substituted by alkyl; and
R⁴ is hydrogen or alkyl.

[18] The 5-membered heterocyclic compound or a pharmaceutically acceptable salt thereof according to the above [17],
wherein R² is (1) carboxyalkyl, (2) carbamoylalkyl, (3) mono- or di-alkylcarbamoylalkyl or (4) alkoxycarbonylalkyl; and
R³ is (1) benzothienyl which may be substituted by halogen, (2) phenyl which may be substituted by a substituent(s) selected from the group consisting of halogen, alkylthio, alkyl, alkoxy and dialkylamino, (3) pyridyl which may be substituted by a substituent(s) selected from the group consisting of alkyl, alkoxy and dialkylamino, (4) pyrimidinyl which may be substituted by alkoxy or dialkylamino, (5) thienyl which may be substituted by one or two alkyl(s), (6) thieno[3,2-b]pyridyl, (7) benzofuryl, (8) dihydrobenzofuryl or (9) indolyl which may be substituted by alkyl.

[19] The 5-membered heterocyclic compound or a pharmaceutically acceptable salt thereof according to the above [17],
wherein R² is carboxyalkyl or alkoxycarbonylalkyl; and
R³ is (1) benzothienyl which may be substituted by halogen, (2) phenyl which may be substituted by a substituent(s) selected from the group consisting of halogen, alkylthio, alkoxy and dialkylamino, (3) pyridyl which may be substituted by a substituent(s) selected from the group consisting of alkyl, alkoxy and dialkylamino, (4) pyrimidinyl which may be substituted by dialkylamino, (5) thienyl which may be substituted by one or two alkyl(s), (6) thieno[3,2-b]pyridyl or (7) indolyl which may be substituted by alkyl.

[20] The 5-membered heterocyclic compound or a pharmaceutically acceptable salt thereof according to any one of the above [17] to [19], wherein $R^2$ is carboxymethyl or alkoxycarbonylmethyl.

[21] The 5-membered heterocyclic compound or a pharmaceutically acceptable salt thereof according to any one of the above [17] to [20], wherein ring A is furan or thiophen.

[22] A compound selected from the group consisting of the compounds described in the examples and preferable examples in the specification, or a pharmaceutically acceptable salt thereof.

[23] A medicine comprising the 5-membered heterocyclic compound or a pharmaceutically acceptable salt thereof according to any one of the above [10] to [22].

[24] A large conductance calcium-activated K channel opener comprising the 5-membered heterocyclic compound or a pharmaceutically acceptable salt thereof according to any one of the above [10] to [22] as an active ingredient.

[25] A large conductance calcium-activated K channel opener according to any one of the above [1] to [9] and [24], which is for the prophylaxis and/or treatment of pollakiuria or urinary incontinence.

[26] A 5-membered heterocyclic compound of the formula (I):

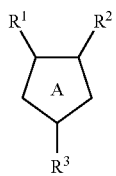

(I)

wherein ring A is a ring represented by any one of the formulae:

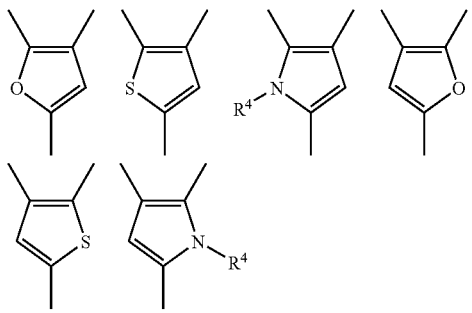

$R^1$ is a substituted or unsubstituted aryl, a substituted or unsubstituted heterocycle or a substituted or unsubstituted heterocycle-substituted carbonyl;

$R^2$ is hydrogen, a halogen, carboxy, a substituted or unsubstituted amino, a substituted or unsubstituted alkyl, an alkoxycarbonyl, a substituted or unsubstituted alkenyl or a cycloalkyl;

$R^3$ is a substituted or unsubstituted aryl, a substituted or unsubstituted heterocycle or a substituted or unsubstituted alkyl; and $R^4$ is hydrogen or a substituted or unsubstituted alkyl;

or a pharmaceutically acceptable salt thereof.

[27] The 5-membered heterocyclic compound or a pharmaceutically acceptable salt thereof according to the above [26], wherein $R^1$ is (1) an aryl which may be substituted by a substituent(s) selected from the group consisting of nitro, amino, hydroxy, carbamoyl, cyano, carboxy, trifluoromethyl, alkoxycarbonyl, halogen, alkyl, hydroxyalkyl, alkoxy, alkoxyalkoxy, mono- or di-alkylamino, mono- or di-alkanoylamino, alkylthio, alkylsulfonyl, alkylsulfinyl, sulfamoyl, mono- or di-alkylsulfamoyl, alkylsulfonylamino and phenylalkoxy, (2) a heterocycle which may be substituted by a substituent(s) selected from the group consisting of nitro, hydroxy, formyl, carbamoyl, cyano, amino, carboxy, alkoxycarbonyl, halogen, alkyl, hydroxyalkyl, alkoxy, mono- or di-alkylamino, mono- or di-alkanoylamino, alkylthio, alkylsulfonyl, alkylsulfinyl, sulfamoyl and mono- or di-alkylsulfamoyl, or (3) a heterocycle-substituted carbonyl which may be substituted by a substituent(s) selected from the group consisting of nitro, hydroxy, carbamoyl, cyano, carboxy, alkoxycarbonyl, halogen, alkyl, hydroxyalkyl, alkoxy, alkanoyl, mono- or di-alkylamino, mono- or di-alkanoylamino, alkylthio, alkylsulfonyl, alkylsulfinyl, sulfamoyl and mono- or di-alkylsulfamoyl;

$R^2$ is (1) hydrogen, (2) halogen, (3) carboxy, (4) amino which may be substituted by a substituent(s) selected from the group consisting of formyl, alkyl, alkanoyl, alkylsulfonyl and alkoxycarbonyl, (5) an alkyl which may be substituted by a substituent(s) selected from the group consisting of halogen, hydroxy, cyano, carboxy, carbamoyl, amino, aminosulfonyl, amidinothio, mono- or di-alkylamino, alkanoylamino, alkylsulfonylamino, hydroxyamino, mono- or di-alkylcarbamoyl, trifluoromethyl, alkoxy, alkylthio, alkylsulfinyl, alkylsulfonyl, alkylsulfonylamino, hydroxycarbamoyl, hydroxycarbamoyl which is substituted by one or two alkyl (s), alkylsulfonylcarbamoyl, sulfamoyl, mono- or di-alkylsulfamoyl, alkoxycarbonyl, heterocycle, heterocycle-substituted carbamoyl, heterocycle-substituted alkylcarbamoyl and heterocycle-substituted sulfonylcarbamoyl, (6) alkoxycarbonyl, (7) alkenyl which may be substituted by carboxy or alkoxycarbonyl, or (8) cycloalkyl;

R3 is (1) an aryl which may be substituted by a substituent (s) selected from the group consisting of cyano, nitro, amino, halogen, trifluoromethyl, carboxy, hydroxy, carbamoyl, mono- or di-alkylamino, aminoalkyl, mono- or di-alkylaminoalkyl, mono- or di-alkylcarbamoyl, alkyl, hydroxyalkyl, alkoxy, alkoxycarbonyl, alkanoyl, alkanoyloxy, alkanoyloxyalkyl, sulfo, alkylthio, alkylthioalkyl, alkylsulfonyl, sulfamoyl, mono- or di-alkylsulfamoyl and alkylsulfinyl, (2) a heterocycle which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (3) an alkyl which may be substituted by a substituent(s) selected from the group consisting of hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle; and $R^4$ is (1) hydrogen or (2) an alkyl which may be substituted by mono- or di-alkylamino.

DESCRIPTION OF THE PREFERRED EMBODIMENTS

The "alkyl", and the alkyl in "alkylthio", "alkylsulfinyl" and "alkylsulfonyl" are exemplified by a straight or branched $C_{1-6}$ alkyl, more specifically, by methyl, ethyl, propyl, isopropyl, butyl, isobutyl, pentyl, hexyl, etc. A $C_{1-4}$ alkyl is preferred.

The "alkoxy", and the alkoxy in "alkoxycarbonyl" are exemplified by a straight or branched $C_{1-6}$ alkoxy, more specifically, by methoxy, ethoxy, propoxy, isopropoxy, butoxy, isobutoxy, pentoxy, hexoxy, etc. A $C_{1-4}$ alkoxy is preferred.

The "alkenyl" is exemplified by a straight or branched $C_{2-7}$ alkenyl, more specifically, by vinyl, allyl, 3-butenyl, 2-pentenyl, 3-hexenyl, etc. It is preferably a $C_{2-5}$ alkenyl.

The "alkanoyl" is exemplified by a straight or branched $C_{2-7}$ alkanoyl, more specifically, by acetyl, propionyl, butyryl, isobutyryl, pentanoyl, hexanoyl, etc. It is preferably a $C_{2-5}$ alkanoyl.

The "cycloalkyl" is exemplified by a $C_{3-8}$ cycloalkyl, preferably a $C_{3-6}$ cycloalkyl.

The "halogen" is exemplified by fluorine, chlorine, bromine, iodine, etc., preferably fluorine, chlorine.

The "aryl" is exemplified by monocyclic, bicyclic or tricyclic $C_{6-14}$ aryl, specifically, phenyl, naphthyl, phenanthryl, anthryl, etc. Phenyl and naphthyl are preferred.

The "heterocycle" and the heterocycle in "heterocycle-substituted carbonyl" are exemplified by a monocyclic, bicyclic or tricyclic 5 to 14-membered heterocycle, which may be partially or wholly saturated, containing 1 to 4 hetero atom(s) selected from nitrogen, oxygen and sulfur, and the like.

The monocyclic heterocycle is preferably exemplified by a 5 to 7-membered heterocycle and may be partially or wholly saturated, containing 1 to 4 hetero atom(s) selected from nitrogen, oxygen and sulfur, and it is specifically exemplified by furyl, thienyl, thiazolyl, thiazolidinyl, isothiazolyl, oxazolyl, isoxazolyl, pyrrolidinyl, pyrrolyl, imidazolyl, pyrazolyl, triazolyl, tetrazolyl, pyranyl, pyridyl, pyrazinyl, pyrimidinyl, triazinyl, piperidyl, piperadinyl and morpholyl, etc.

The bicyclic heterocycle is preferably exemplified by a bicyclic heterocycle in which two of the same or different monocyclic heterocycles above are fused, or a bicyclic heterocycle in which the above monocyclic heterocycle and benzene are fused, and it is specifically exemplified by indolyl, dihydroindolyl, isoindolyl, quinolyl, tetrahydroquinolyl, isoquinolyl, naphthylidyl, quinoxalyl, dihydroquinoxalyl, phthaladinyl, quinazolinyl, quinolinyl, dihydroquinolinyl, benzofuryl, isobenzofuryl, dihydrobenzofuryl, benzothienyl, benzodioxanyl, chromenyl, indolidinyl, purinyl, quinuclidinyl, trihydrocyclopentathienyl, benzothianyl, benzothiazolyl, imidazopyridyl, indolinyl, chromanyl, thiophenopyridyl, furanopyridyl, dihydrobenzopyranyl and 3,4-methylenedioxyphenyl, etc.

The tricyclic heterocycle is preferably exemplified by a tricyclic heterocycle in which the above monocyclic heterocycle and the above bicyclic heterocycle are fused, or a tricyclic heterocycle in which the above monocyclic heterocycle and two benzenes are fused, and it is specifically exemplified by carbazolyl, carbolinyl, xanthenyl, phenanthridinyl, acridinyl, perimidinyl, phenazinyl, and phenoxazinyl, etc.

The preferred heterocycle is exemplified by a heterocycle having at least one aromatic ring. It is specifically exemplified by furyl, thienyl, thiazolyl, isoxazolyl, pyrrolidinyl, pyrrolyl, pyridyl, pyrazinyl, pyrimidinyl, tetrazolyl, indolyl, quinolyl, isoquinolyl, benzofuryl, benzothienyl, dihydrobenzofuryl, thienopyridyl and benzodioxanyl, etc. The preferred heterocycle of $R^1$ is exemplified by thienyl and pyridyl, etc. The preferred heterocycle of $R^3$ is exemplified by benzothienyl, pyridyl, pyrimidinyl, thienyl, thieno[3.2-b]pyridyl, indolyl, benzofuryl and dihydrobenzofuryl, etc., and particularly preferably benzo[b]thienyl, pyridyl, pyrimidinyl, thienyl, thieno[3.2-b]pyridyl and indolyl, etc.

The substituent for the "substituted aryl" of $R^1$ is exemplified by nitro, amino, hydroxy, carbamoyl, cyano, carboxy, trifluoromethyl, alkoxycarbonyl, halogen, alkyl, hydroxyalkyl, alkoxy, alkoxyalkoxy, mono- or di-alkylamino, mono- or di-alkanoylamino, alkylthio, alkylsulfonyl, alkylsulfinyl, sulfamoyl, mono- or di-alkylsulfamoyl, alkylsulfonylamino and phenylalkoxy, etc. The aryl may be substituted by 1 to 3 same or different substituent(s) as mentioned above. The preferred substituent(s) is exemplified by a halogen such as chlorine and fluorine, etc.

The substituent for the "substituted heterocycle" of $R^1$ is exemplified by nitro, hydroxy, formyl, carbamoyl, cyano, amino, carboxy, alkoxycarbonyl, halogen, alkyl, hydroxyalkyl, alkoxy, mono- or di-alkylamino, mono- or di-alkanoylamino, alkylthio, alkylsulfonyl, alkylsulfinyl, sulfamoyl and mono- or di-alkylsulfamoyl, etc. The heterocycle may be substituted by 1 to 3 same or different substituent(s) as mentioned above. The preferred substituent(s) is exemplified by a halogen such as chlorine and fluorine, alkyl, etc.

The substituent on the heterocycle for the "substituted heterocycle-substituted carbonyl" of $R^1$ is exemplified by nitro, hydroxy, formyl, carbamoyl, cyano, amino, carboxy, alkoxycarbonyl, halogen, alkyl, hydroxyalkyl, alkoxy, alkanoyl, mono- or di-alkylamino, mono- or di-alkanoylamino, alkylthio, alkylsulfonyl, alkylsulfinyl, sulfamoyl and mono- or di-alkylsulfamoyl, etc. The heterocycle-substituted carbonyl may be substituted by 1 to 3 same or different substituent(s) as mentioned above. The preferred substituent(s) is exemplified by a halogen such as chlorine and fluorine, etc.

The substituent for the "substituted amino" of $R^2$ is exemplified by formyl, alkyl, alkanoyl, alkylsulfonyl and alkoxycarbonyl, etc. The amino may be substituted by 1 or 2 same or different substituent(s) as mentioned above.

The substituent for the "substituted alkyl" and "substituted alkenyl" of $R^2$ is exemplified by halogen, hydroxy, cyano, carboxy, carbamoyl, amino, aminosulfonyl, amidinothio, mono- or di-alkylamino, alkanoylamino, alkylsulfonylamino, hydroxyamino, mono- or di-alkylcarbamoyl, trifluoromethyl, alkoxy, alkylthio, alkylsulfinyl, alkylsulfonyl, alkylsulfonylamino, hydroxycarbamoyl, hydroxycarbamoyl which is substituted by 1 or 2 alkyl(s), alkylsulfonylcarbamoyl, sulfamoyl, mono- or di-alkylsulfamoyl, alkoxycarbonyl, heterocycle, heterocycle-substituted carbamoyl, heterocycle-substituted alkylcarbamoyl and heterocycle-substituted sulfonylcarbamoyl, etc. The particularly preferred substituent is exemplified by carboxy, alkoxycarbonyl, carbamoyl, mono- or di-alkylcarbamoyl, tetrazolyl, etc. The alkyl and alkenyl may be each substituted by 1 to 3 same or different substituent (s) as mentioned above. The particularly preferred example of the "substituted alkyl" of $R^2$ include carboxymethyl, alkoxycarbonylmethyl, carbamoylmethyl, mono- or di-alkylcarbamoylmethyl and tetrazolylmethyl, etc.

The substituent for the "substituted aryl" of $R^3$ is exemplified by cyano, nitro, amino, halogen, trifluoromethyl, carboxy, hydroxy, carbamoyl, mono- or di-alkylamino, aminoalkyl, mono- or di-alkylaminoalkyl, mono- or di-alkylcarbamoyl, alkyl, hydroxyalkyl, alkoxy, alkoxycarbonyl, alkanoyl, alkanoyloxy, alkanoyloxyalkyl, sulfo, alkylthio, alkylthioalkyl, alkylsulfonyl, sulfamoyl, mono- or di-alkylsulfamoyl, alkylsulfinyl, trimethylene and tetramethylene, etc. The aryl may be substituted by 1 to 3 same or different substituent(s) as mentioned above. The preferred substituent is exemplified by amino, halogen, alkyl, alkylthio, alkoxy and mono- or di-alkylamino, etc., particularly preferably halogen, alkylthio, alkoxy and dialkylamino, etc. When $R^3$ is a substituted phenyl, the preferred substituted position of the substituent(s) includes a para-position and a meta-position. For example, the 2 or more above-mentioned substituents may be substituted at the para-position and the meta-position, or else, a divalent group (an alkylene such as trimethylene, tetramethylene, etc.) may be substituted at the para-position and the meta-position.

The substituent for the "substituted heterocycle" of $R^3$ is exemplified by oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkoxy, alkoxycarbonyl, alkanoyl, sulfo, alkylthio, alkylsulfonyl, sulfamoyl, mono- or di-alkylsulfamoyl, alkylsulfinyl, heterocycle, trimethylene and tetramethylene, etc. The heterocycle may be substituted by 1 to 3 same or different substituent(s) as mentioned above. The preferred substituent(s) is exemplified by amino, halogen, alkyl, alkylthio, alkoxy and mono- or di-alkylamino, etc. The preferred substituted position of the substituted heterocycle includes a β-position and a γ-position (the second or the third position from the binding position) from the binding position to the 5-membered heterocycle of the formula (1). For example, the above-mentioned 2 or more substituents may be substituted at the β-position and the γ-position, or else, a divalent group (an alkylene such as trimethylene and tetramethylene, etc.) may be substituted at the β-position and the γ-position.

The substituent for the "substituted alkyl" of $R^3$ is exemplified by hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle, etc. The alkyl may be substituted by 1 to 3 same or different substituent(s) as mentioned above.

The substituent for the "substituted alkyl" of $R^4$ is exemplified by mono- or di-alkylamino, etc. The alkyl may be substituted by the same or different 1 or 2 respective substituent(s) as mentioned above.

In the 5-membered heterocyclic compound (1) of the present invention, an optical isomer or a tautomer based on an asymmetric carbon may be present depending on a kind of a substituent(s). Any of the optical isomer, the tantomer and a mixture thereof may be encompassed in the present invention.

The 5-membered heterocyclic compound (1) of the present invention or a pharmaceutically acceptable salt thereof can be used for the present medical use in the free form or in the form of a pharmaceutically acceptable salt. Examples of pharmaceutically acceptable salts of the compound (1) may include, for example, inorganic acid salts such as hydrochloride, sulfate, phosphate or hydrobromide, and organic acid salts such as acetate, fumarate, oxalate, citrate, methanesulfonate, benzenesulfonate, tosylate or maleate. In addition, in case of compound having an acidic group such as carboxy, salts with a base (for example, alkali metal salts such as a sodium salt and a potassium salt, alkaline earth metal salts such as a calcium salt, organic base salts such as a triethylamine salt, or amino acid salts such as a lysine salt) can be mentioned.

The 5-membered heterocyclic compound (1) of the present invention or a pharmaceutically acceptable salt thereof includes its internal salts, and solvates such as hydrates.

The 5-membered heterocyclic compound (1) of the present invention or a pharmaceutically acceptable salt thereof can be administered orally or parenterally, and used as common pharmaceutical preparations such as tablets, granules, capsules, powders, injection and inhalants with a pharmaceutically acceptable carrier or diluent.

A pharmaceutically acceptable carrier for a preparation of oral administration includes a material commonly used, for example, a binder (such as syrup, Gum Arabic, gelatin, sorbit, tragacanth and polyvinyl pyrrolidone), an excipient (such as lactose, sugar, corn starch, potassium phosphate, sorbit and glycine), a lubricant (such as magnesium stearate, talc, polyethylene glycol and silica), a disintegrator (such as potato starch) and a humectant (such as anhydrous lauryl sodium sulfate).

On the other hand, when the active ingredient of the present invention is administered parenterally, it may be formulated into the form of an injection or a drip infusion by using distilled water for injection, physiological saline, an aqueous glucose solution and the like, or a suppository.

A dose of the 5-membered heterocyclic compound (1) of the present invention or a pharmaceutically acceptable salt thereof may vary depending on an administration route, an age, weight, conditions or a kind or degree of disease of a patient, and generally about 0.1 to 50 mg/kg per day, particularly preferably about 0.3 to 30 mg/kg per day.

The 5-membered heterocyclic compound (1) of the present invention or a pharmaceutically acceptable salt thereof has an excellent large conductance calcium-activated K channel opening activity and hyperpolarizes a membrane electric potential of cells, so that it may be used as an agent for a prophylactic, relief and/or treatment of, for example, hypertension, premature birth, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, male-pattern baldness, erectile dysfunction, diabetes, diabetic peripheral nerve disorder, other diabetic complication, sterility, urolithiasis and pain accompanied thereby, pollakiuria, urinary incontinence, nocturnal enuresis, asthma, chronic obstructive pulmonary disease (COPD), cough accompanied by asthma or chronic obstructive pulmonary disease (COPD), cerebral apoplexy, cerebral ischemia, traumatic encephalopathy, and the like.

The 5-membered heterocyclic compound (1) of the present invention can be prepared by, for example, the following [Method A] to [Method G].

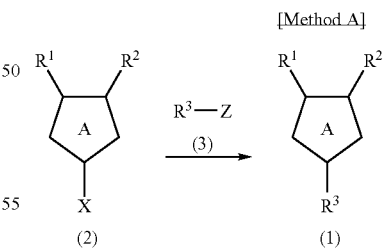

[Method A]

wherein X is a reactive residue, Z is —B(OR)$_2$, —B(OH)$_2$ or —Sn(R)$_3$, R is alkyl, and Ring A, $R^1$, $R^2$ and $R^3$ have the same meanings as defined above.

Compound (1) can be produced by reacting compound (2) and compound (3) in the presence of a palladium catalyst. The palladium catalyst is exemplified by a zero (0) valent or divalent palladium catalyst such as tetrakis(triphenylphosphine) palladium (0), bis(triphenylphosphine) palladium (II) chloride and palladium (II) acetate, and they are suitably used. When the reaction is carried out by using compound (3) wherein Z is —B(OR)$_2$ or —B(OH)$_2$, it is preferred to add a base. The base is exemplified by inorganic bases such as an alkali metal carbonate, an alkali metal hydroxide, an alkali metal phosphate and an alkali metal fluoride, or organic bases such as triethylamine, and they are suitably used. The present reaction can be carried out in a suitable solvent or without any solvent. The solvent, it may be any solvent which does not cause any bad effect on the reaction, it is exemplified by dimethoxyethane, tetrahydrofuran, dimethylformamide, methanol, ethanol, toluene, benzene, chloroform or a mixed solvent thereof, and they are suitably used. The present reaction suitably proceeds at 60 to 150° C., particularly preferably at 80 to 120° C. The reactive residue of X may be preferably a halogen, etc.

The starting compound (2) can be produced, for example, as mentioned below.

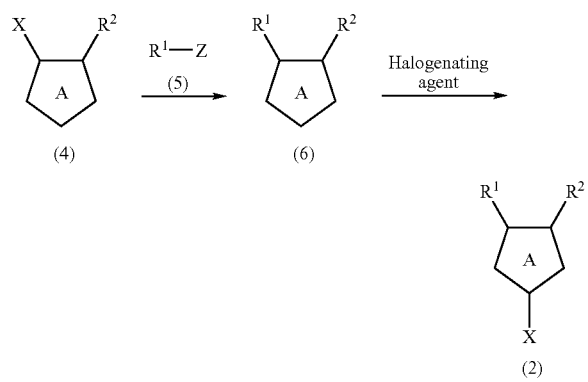

wherein Ring A, X, Z, R$^1$ and R$^2$ have the same meanings as defined above.

Compound (6) can be produced by reacting compound (4) and compound (5) in the same manner as in the above-mentioned [Method A]. Compound (6) can also be obtained by reacting compound (4) wherein X is —B(OR)$_2$, —B(OH)$_2$ or —Sn(R)$_3$ with compound (5) wherein Z is a reactive residue.

Subsequently, compound (2) can be produced by halogenating compound (6) by using a halogenating agent according to the conventional manner and the like. The halogenating agent is exemplified by bromine, chlorine, iodine, [bis(trifluoroacetoxy)iodo]benzene, N-bromosuccinic imide, etc., and they can be suitably used. The present reaction can proceed suitably according to the conventional manner at 0° C. to 30° C.

In the present [Method A], it is explained by a method in which R$^1$ and R$^3$ are introduced in this order into Ring A to which R$^2$ has been introduced, but it is also possible to introduce in the order of R$^3$ and R$^1$, or to introduce another substituent at the position of R$^2$ and finally converting it to R$^2$.

This [Method A] can be suitably applied to compound (1) wherein Ring A is furan and thiophene.

[Method B]

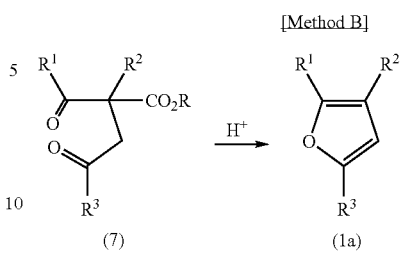

wherein R, R$^1$, R$^2$ and R$^3$ have the same meanings as defined above.

Compound (1a) wherein Ring A is furan can be produced by treating compound (7) with an acid. The acid is exemplified by hydrochloric acid, sulfuric acid, nitric acid, phosphoric acid, methanesulfonic acid, trifluoroacetic acid, etc. As a reaction solvent, any solvent may be used so long as it does not cause any bad effect on the reaction, and, for example, a solvent which can dissolve compound (7) and the above-mentioned acid can be used, and specifically, acetic acid, etc. may be suitably used. As a reaction temperature, a range from room temperature to the boiling point of the solvent may be mentioned. In the above-mentioned preparation method, the reaction in which R$^1$ and R$^2$ have the above-mentioned configuration is shown, but compound in which the bonding sites of R$^1$ and R$^2$ are exchanged to each other can be also prepared in the same manner as mentioned above.

The starting compound (7) can be produced, for example, as mentioned below.

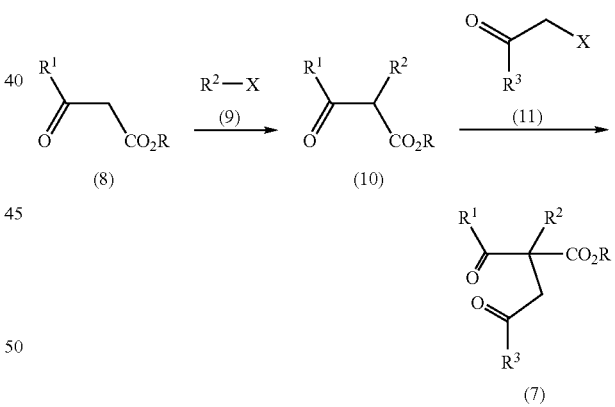

wherein X, R, R$^1$, R$^2$ and R$^3$ have the same meanings as defined above.

Compound (10) can be produced by reacting compound (8) with compound (9) in the presence of a base according to the conventional manner. Subsequently, compound (10) is reacted with compound (11) in the presence of a base according to the conventional manner to obtain the starting compound (7). In the present reaction, compound (11) may be reacted with compound (8) first, and then, the resulting compound is reacted with compound (9).

[Method C]

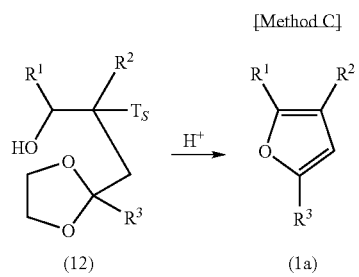

wherein $R^1$, $R^2$ and $R^3$ have the same meanings as defined above and Ts is p-toluenesulfonyl.

Compound (1a) wherein Ring A is furan can be produced by treating compound (12) with an acid according to the conventional manner ("Comprehensive Heterocyclic Chemistry", Vol. 4, A. Katritzky, et al., Pergamon Press Ltd., p. 661-662, 1984). In the above-mentioned preparation method, the reaction in which $R^1$ and $R^2$ have the above-mentioned configuration is shown, but compound in which the bonding sites of $R^1$ and $R^2$ are exchanged to each other can be also prepared in the same manner as mentioned above.

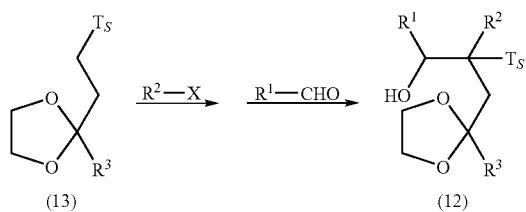

wherein $R^1$, $R^2$, $R^3$, X and Ts have the same meanings as defined above.

The starting compound (12) can be produced by reacting compound (13) with $R^2$—X and $R^1$—CHO in this order in the presence of a base according to the conventional manner ("Comprehensive Heterocyclic Chemistry" Vol. 4, A. Katritzky et al., Pergamon Press Ltd., p. 661-662, 1984).

[Method D]

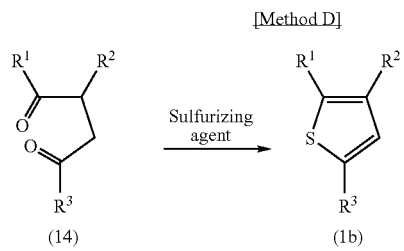

wherein R, $R^1$, $R^2$ and $R^3$ have the same meanings as defined above.

Compound (1b) wherein Ring A is thiophene can be produced by reacting a sulfurizing agent to compound (14) according to the conventional manner ("Comprehensive Heterocyclic Chemistry" Vol. 4, A. Katritzky et al., Pergamon Press Ltd., p. 885-887, 1984). The sulfurizing agent is exemplified by hydrogen sulfide, phosphorus trisulfide, Lawesson's reagent (2,4-bis(4-methoxyphenyl)-1,3-dithia-2,4-diphosphetan-2,4-disulfide), etc. and they are suitably used. Compound (14) can be also produced, for example, from the starting compound (7) of [Method B]. In the above-mentioned preparation method, the reaction in which $R^1$ and $R^2$ have the above-mentioned configuration is shown, but compound in which the bonding sites of $R^1$ and $R^2$ are exchanged to each other can be also prepared in the same manner as mentioned above.

[Method E]

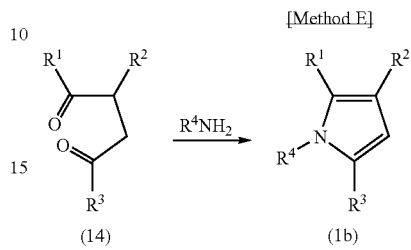

wherein R, $R^1$, $R^2$, $R^3$ and $R^4$ have the same meanings as defined above.

Compound (1b) wherein Ring A is pyrrole can be produced by reacting compound (14) with $R^4NH_2$ or its salt according to the conventional manner ("Comprehensive Heterocyclic Chemistry" Vol. 4, A. Katritzky et al., Pergamon Press Ltd., p. 329-330, 1984). The $R^4NH_2$ or its salt is exemplified by ammonia, ammonium carbonate, ammonium acetate, monoalkylamine, etc., and they can be used. Compound (1b) wherein $R^4$ is hydrogen can be also produced by subjecting to the reaction using an amide derivative such as acetic amide or a sulfonamide derivative in place of $R^4NH_2$ according to the conventional manner, and then, subjecting to hydrolysis. In the above-mentioned preparation method, the reaction in which $R^1$ and $R^2$ have the above-mentioned configuration is shown, but compound in which the bonding sites of $R^1$ and $R^2$ are exchanged to each other can be also prepared in the same manner as mentioned above.

[Method F]

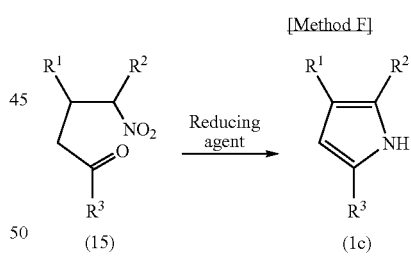

wherein $R^1$, $R^2$ and $R^3$ have the same meanings as defined above.

Compound (1c) wherein Ring A is pyrrole can be produced by reacting a reducing agent on compound (15) according to the conventional manner. The reducing agent is exemplified by a disulfide such as diphenyldisulfide, and a phosphine such as tri-n-butylphosphine, and they can be used in combination. The reaction temperature may vary depending on a kind of the reducing agent, and is, for example, from 0° C. to a boiling point of the solvent. In the above-mentioned preparation method, the reaction in which $R^1$ and $R^2$ have the above-mentioned configuration is shown, but compound in which the bonding sites of $R^1$ and $R^2$ are exchanged to each other can be also prepared in the same manner as mentioned above.

[Method G]

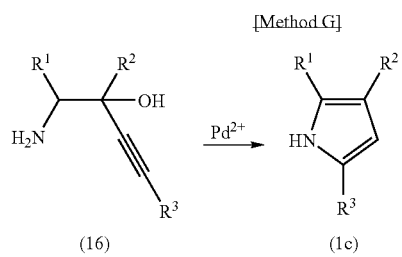

wherein $R^1$, $R^2$ and $R^3$ have the same meanings as defined above.

Compound (1c) wherein Ring A is pyrrole can be produced by acting a palladium catalyst on compound (16) ("Comprehensive Heterocyclic Chemistry" Vol. 4, A. Katritzky et al., Pergamon Press Ltd., p. 321, 1984). In the above-mentioned preparation method, the reaction in which $R^1$ and $R^2$ have the above-mentioned configuration is shown, but a compound in which the bonding sites of $R^1$ and $R^2$ are exchanged to each other can be also prepared in the same manner as mentioned above.

In the 5-membered heterocyclic compound (1) produced by the above-mentioned preparation methods, its functional group may be converted into the other functional group, if necessary. Conversion between the functional groups can be carried out according to the conventional manner, and methods as disclosed in, for example, "Comprehensive Organic Tranformations" Richard C. Larock, VCH Publishers Inc., 1989, "Comprehensive Organic Synthesis" Vol. 1-9, Barry M. Trost et al., Pergamon Press Ltd., 1991, "Organic Reactions" John Wiley & Sons Ltd., 1963, etc. can be used. There are mentioned conversion from carboxy to hydroxy, Curtius rearrangement from carboxy to amino, conversion from carboxy to amide, condensation of amide and Grignard reagent, Friedel-Crafts reaction, Vilsmeier reaction and the like, and specific methods are as mentioned in the following methods (a) to (u).

Method (a):
Compound (1) wherein $R^2$ is a halogen can be produced by reacting compound wherein the corresponding $R^2$ is hydrogen and a halogenating agent. The halogenating agent is exemplified by bromine, chlorine, iodine, [bis(trifluoroacetoxy)iodo]benzene, N-bromosuccinic imide, etc., and they are suitably used. The present reaction suitably proceeds at 0° C. to 30° C.

Method (b):
Compound (1) wherein $R^1$ is an aryl which may be substituted or a heterocycle which may be substituted can be produced by reacting a compound wherein the corresponding $R^1$ is a halogen and a trialkyl tin compound having an aryl which may be substituted or a heterocycle which may be substituted in the presence of a catalyst. The catalyst is exemplified by a zero-valent or divalent palladium series catalyst such as bis(triphenylphosphine) palladium (II) chloride, palladium (II) acetate, tetrakis (triphenylphosphine) palladium (0), etc., and they are suitably sued. The present reaction further suitably proceeds by the addition of a zinc salt such as zinc chloride, zinc bromide, zinc iodide, etc. The present reaction suitably proceeds at 50° C. to 120° C.

The present reaction can be also carried out by using a boric acid compound or a borate compound in place of the trialkyl tin compound in the presence of a base. The palladium series catalyst and the base are exemplified by either of those as mentioned in the above-mentioned Method A, and they are suitably used. The present reaction suitably proceeds at 60° C. to 120° C.

Method (c):
Compound (1) wherein $R^4$ is an alkyl which may be substituted can be produced by reacting a compound wherein the corresponding $R^4$ is hydrogen with an alkyl halide (alkyl iodide, alkyl chloride, alkyl bromide, etc.) or an alkylsulfonate (alkyltrifluoromethane sulfonate, alkylmethane sulfonate, etc.) both of which may be substituted in the presence of a base. The base is exemplified by an alkali metal hydride, an alkali metal carbonate, an alkali metal alkoxide, alkali metal hydroxide, etc., and they are suitably used. The present reaction suitably proceeds at 30° C. to 80° C.

Method (d):
Compound (1) wherein $R^2$ is formylamino or N-alkyl-N-formylamino can be produced by reacting a compound wherein the corresponding $R^2$ is amino or N-alkylamino and an alkyl formate (methyl ester, ethyl ester, etc.). The present reaction suitably proceeds at 60° C. to 100° C.

Method (e):
Compound (1) wherein $R^2$ is N-methylamino, N-alkyl-N-methylamino or N-ethylamino can be produced by reacting compound wherein the corresponding $R^2$ is formylamino, N-alkyl-N-formylamino or N-acetylamino in the presence of a reducing agent.

The reducing agent is exemplified by a borane complex (for example, borane-dimethylsulfide complex, etc.) or lithium aluminum hydride, and they are suitably used. The present reaction suitably proceeds at 0° C. to 60° C.

Method (f):
Compound (1) wherein $R^2$ is alkoxycarbonylamino can be produced by reacting a compound wherein the corresponding $R^2$ is amino and an alkoxycarbonyl halide in the presence of a base. The base is exemplified by pyridine, triethylamine, an alkali metal carbonate, an alkali metal alkoxide, an alkali metal hydride, etc., and they are suitably used. The present reaction suitably proceeds at 0° C. to 50° C.

Method (g):
Compound (1) wherein $R^2$ is hydroxyalkyl can be produced by reacting compound wherein the corresponding $R^2$ is hydrogen and formaldehyde in the presence of a base. The base is exemplified by an alkali metal carbonate, an alkali metal alkoxide, triethylamine, etc., and they are suitably used. The present reaction suitably proceeds at 60° C. to 120° C.

Method (h):
Compound (1) wherein $R^2$ is a halogenoalkyl can be produced by reacting a compound wherein the corresponding $R^2$ is a hydroxyalkyl with a halogenating agent. The halogenating agent is exemplified by thionyl chloride, thionyl bromide, etc., and they are suitably used. The present reaction suitably proceeds at 0° C. to 50° C.

Method (i):
Compound (1) wherein $R^2$ is an alkoxyalkyl can be produced by reacting a compound wherein the corresponding $R^2$ is a halogenoalkyl and an alkanol. The alkanol is exemplified by methanol, ethanol, etc., and they are suitably used. The present reaction suitably proceeds at 30° C. to 80° C.

Method (j):
Compound (1) wherein $R^2$ is an alkylthioalkyl can be produced by reacting a compound wherein the corresponding $R^2$ is a halogenoalkyl and an alkylsulfide salt. The alkylsulfide salt is exemplified by an alkali metal salt such as sodium methylsulfide, etc., and they are suitably used. The present reaction is preferably carried out in the presence of a base. The base is exemplified by triethylamine, pyridine, an alkali metal carbonate, an alkali metal hydroxide, an alkali metal alkoxide, etc., and they are suitably used. The present reaction suitably proceeds at 0° C. to 60° C.

Method (k):
Compound (1) wherein $R^2$ is an alkylsulfinylalkyl or alkylsulfonylalkyl can be produced by reacting a compound wherein the corresponding $R^2$ is an alkylthioalkyl with an oxidizing agent. The oxidizing agent is exemplified by metachloroperbenzoic acid, aqueous hydrogen peroxide, etc., and they are suitably used. The present reaction suitably proceeds at −20° C. to 30° C.

Method (l):
Compound (1) wherein $R^2$ is a carboxyalkyl can be produced by hydrolyzing compound wherein the corresponding $R^2$ is an alkoxycarbonylalkyl in the presence of a base. The base is exemplified by alkali metal hydroxide, etc., and they are suitably used. The present reaction suitably proceeds at 30° C. to 60° C.

Method (m):
Compound (1) wherein $R^3$ is a heterocycle substituted by sulfo can be produced by reacting compound wherein the corresponding $R^3$ is unsubstituted heterocycle (provided that it may have other substituent(s) than the position of the heterocyclic ring onto which the sulfo group is substituted) and a halogenosulfonic acid (chlorosulfonic acid, etc.), and then, treating the resulting compound with an aqueous basic solution (aqueous ammonia, etc.). The present reaction suitably proceeds at 0° C. to 50° C.

Method (n):
Compound (1) wherein $R^3$ is a heterocycle substituted by sulfamoyl can be produced by treating compound wherein the corresponding $R^3$ is a heterocycle substituted by chloro-sulfonyl obtained by the above-mentioned Method with ammonia. The present reaction suitably proceeds at 0° C. to 60° C.

Method (o):
Compound (1) wherein $R^1$ or $R^3$ is a heterocycle substituted by a hydroxyalkyl can be produced by treating a compound wherein the corresponding $R^1$ or $R^3$ is a heterocycle substituted by an alkoxycarbonyl with a reducing agent. The reducing agent is exemplified by lithium aluminum hydride, lithium borohydride, a borane complex (for example, borane•dimethylsulfide complex, etc.), etc., and they are suitably used. The present reaction suitably proceeds at 0° C. to 60° C.

Method (p):
Compound (1) wherein $R^3$ is pyridyl substituted by a mono- or di-alkylamino, or pyrazinyl substituted by a mono- or di-alkylamino can be produced by reacting compound wherein the corresponding $R^3$ is a halogenopyridyl or halogenopyrazinyl and a corresponding mono- or di-alkylamine. The present reaction suitably proceeds at 30° C. to 120° C.

Method (q):
Compound (1) wherein $R^3$ is pyrimidinyl substituted by a mono- or di-alkylamino can be produced by oxidizing a compound wherein the corresponding $R^3$ is an alkylthiopyrimidinyl with an oxidizing agent, and subsequently reacting with a mono- or di-alkylamine. The oxidizing agent is exemplified by m-chloroperbenzoic acid, hydrogen peroxide, etc., and they are suitably used. The present reaction suitably proceeds at 30° C. to 120° C.

Method (r):
Compound (1) wherein $R^2$ is a carbamoylalkyl which may be substituted can be produced by reacting a compound wherein the corresponding $R^2$ is a carboxyalkyl and a corresponding amine which may be substituted in the presence of a condensing agent. The condensing agent is exemplified by 3-ethyl-1-(3-dimethylaminopropyl) carbodiimide hydrochloride, cyano diethyl phosphate, etc., and they are suitably used. The present reaction suitably proceeds at 0° C. to 50° C.

Method (s):
Compound (1) wherein $R^2$ is a cyanoalkyl can be produced by reacting a compound wherein the corresponding $R^2$ is a carbamoylalkyl and a dehydrating agent. The dehydrating agent is exemplified by phosphorus oxychloride, acetic anhydride, thionyl chloride, etc., and they are suitably used. The present reaction suitably proceeds at 50° C. to 100° C.

Method (t):
Compound (1) wherein $R^2$ is a tetrazolylalkyl can be produced by reacting a compound wherein the corresponding $R^2$ is a cyanoalkyl and an azide compound. The azide compound is exemplified by sodium azide, trialkyl tin azide, trialkyl silicon azide, etc., and they are suitably used. The present reaction suitably proceeds at 80° C. to 120° C.

Method (u):
Compound (1) wherein $R^2$ is an alkoxycarbonylmethyl can be synthesized by a one-carbon increasing reaction of compound wherein the corresponding $R^2$ is formyl. The one-carbon increasing reagent is exemplified by methyl(methylsulfinylmethyl)sulfide, tosylmethyl isocyanate, diethylphosphonodithiane, diethyl 1-piperidinomethyl phosphonate, etc., and they are suitably used. After reacting with these reagents in the presence of a base, the resultant compound is reacted with an alcohol in the presence of an acid to give an alkoxycarbonylmethyl compound.

The reactions described in the above-mentioned Methods (a) to (u) can be carried out in a solvent which is inactive to the reaction or in the absence of a solvent. The solvent is not specifically limited, and it is exemplified by methylene chloride, chloroform, tetrahydrofuran, methanol, ethanol, isopropanol, dimethylformamide, dimethylsulfoxide, water, ethyl acetate, dimethoxyethane, toluene, benzene, etc., or a mixed solvent of the above-mentioned solvents.

In the above-mentioned preparations, the protection and deprotection of a functional group can be carried out, if necessary. As a protective group for the functional group, those used in the general organic synthetic chemistry can be used, and examples thereof include those described in "Protective Groups in Organic Synthesis" T. W. Greene, P. M. Wuts, John Wiley and Sons 1991, etc. The conditions for introduction of the protective group and deprotection are exemplified by those described in the above publication.

In the above-mentioned preparations, the respective compounds and the respective intermediates to be produced can be purified by the usual manner such as column chromatography, recrystallization, etc. The solvent to be used for the recrystallization is exemplified by an alcohol solvent such as methanol, ethanol, 2-propanol, etc., an ether solvent such as diethyl ether, etc., an ester solvent such as ethyl acetate, etc., an aromatic solvent such as toluene, etc., a ketone solvent such as acetone, etc., a hydrocarbon solvent such as hexane, etc., water and the like or a mixed solvent of the above-mentioned solvents. The compound (1) of the present invention can be converted into a pharmaceutically acceptable salt according to the conventional manner, and thereafter, recrystallization, etc., may be carried out.

BEST MODE OF EMBODIMENT OF THE INVENTION

In the following, the present invention will be explained in more detail by referring to Examples, Reference examples and Experimental examples, but the present invention is not limited by Examples, etc.

The following abbreviations used in the present specification have the following means, respectively.

Me: methyl
Et: ethyl
Ph: phenyl
THF: tetrahydrofuran
DMF: N,N-dimethylformamide
DME: dimethoxyethane

EXAMPLE 1

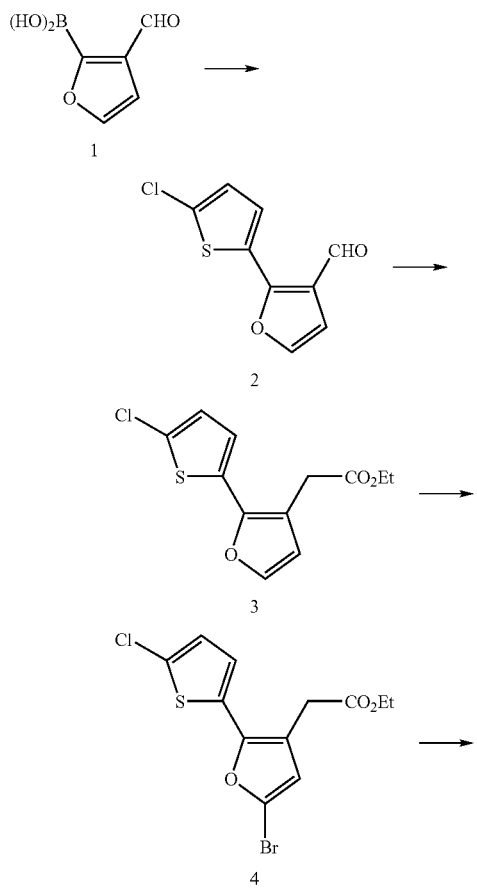

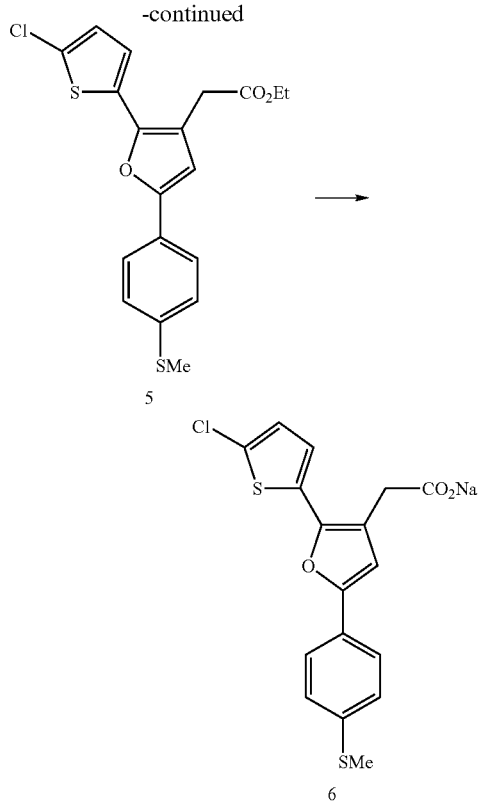

(1) A 2N aqueous sodium carbonate solution (5.5 ml) was added to a mixed solution of compound 1 (0.5 g, 3.6 mmol), 2-bromo-5-chlorothiophene (0.6 ml, 5.5 mmol) and PdCl$_2$(PPh$_3$)$_2$ (250 mg, 0.36 mmol) dissolved in DMF (17 ml). After subjecting to reflux under heating for 3 hours, the mixture was subjected to filtration with Celite. The filtrate was extracted with ethyl acetate, washed with water and brine, dried over anhydrous sodium sulfate and concentrated under reduced pressure. The residue was purified by silica gel column chromatography (hexane/ethyl acetate=20/1) to give compound 2 (215 mg, 28.2%) as powder. MS•APCI (m/z): 227/229 ([M+H+ MeOH−H$_2$O]$^+$)

(2) To a solution of compound 2 (200 mg, 0.94 mmol) dissolved in THF (5 ml) were added methyl(methylsulfinyl-methyl)sulfide (0.3 ml, 2.9 mmol) and Triton B (0.22 ml, 0.5 mmol, 40% methanol solution), and the mixture was refluxed under heating for 4 hours. The reaction mixture was poured into 0.5N hydrochloric acid, and extracted with ethyl acetate. The extract was washed with brine, dried over anhydrous sodium sulfate and concentrated under reduced pressure. The residue was dissolved in a 0.5N hydrochloric acid-ethanol solution (5 ml), and the mixture was refluxed under heating for 1.5 hours. The solvent was removed under reduced pressure, and the residue was extracted with ethyl acetate. The extract was washed with brine, dried over anhydrous magnesium sulfate and concentrated under reduced pressure. The residue was purified by silica gel column chromatography (hexane/ethyl acetate=20/1) to give compound 3 (148 mg, 58.1%) as an oily substance.

MS•APCI (m/z): 271/273 ([M+H]$^+$)

(3) To a solution of compound 3 (68 mg, 0.25 mmol) dissolved in chloroform (5 ml) was added dropwise a solution of bromine (40 mg, 0.25 mmol) dissolved in chloroform (1 ml) under ice-cooling. After an aqueous saturated sodium hydrogen carbonate solution was added to the reaction mixture, the resulting mixture was extracted with ethyl acetate. The extract was washed successively with a 15% aqueous sodium thiosulfate solution and brine, dried over anhydrous sodium sulfate and concentrated under reduced pressure to give crude compound 4 (0.1 g).

(4) To a solution of compound 4 and 4-methylthiophenyl boric acid (75 mg, 45 mmol) dissolved in DME were added PdCl$_2$(PPh$_3$)$_2$ (60 mg, 0.029 mmol) and a 2N sodium carbonate solution (0.86 ml, 1.8 mmol). After the reaction mixture was refluxed under heating for 3 hours, the resulting mixture was subjected to filtration with Celite. The filtrate was extracted with ethyl acetate, washed successively with water and brine, dried over anhydrous sodium sulfate and concentrated under reduced pressure. The residue was purified by silica gel column chromatography (hexane/ethyl acetate=20/1) to give compound 5 (57 mg, 57.9%) as powder.

MS•APCI (m/z): 393/395 ([M+H]$^+$)

(5) To a solution of compound 5 (52 mg, 0.13 mmol) dissolved in ethanol (5 ml) was added a 2N aqueous sodium hydroxide solution, and the mixture was stirred at room temperature overnight. To the reaction mixture was added a 1N hydrochloric acid, and the resulting mixture was extracted with ethyl acetate. The organic layer was washed with brine, dried over anhydrous sodium sulfate and filtered, and the filtrate was concentrated under reduced pressure. The residue was purified by preparative HPLC to give a corresponding carboxylic acid (34 mg, 71%).

MS•ESI (m/z): 363/365 ([M−H]$^+$)

The resulting carboxylic acid (31 mg, 0.085 mmol) was dissolved in methanol (1.5 mmol), and 0.5N sodium methoxide (methanol solution, 0.165 ml, 0.083 mmol) was added thereto. The solvent was removed to give compound 6 (35 mg).

MS•ESI (m/z): 363/365 ([M−Na]$^−$)

EXAMPLE 2

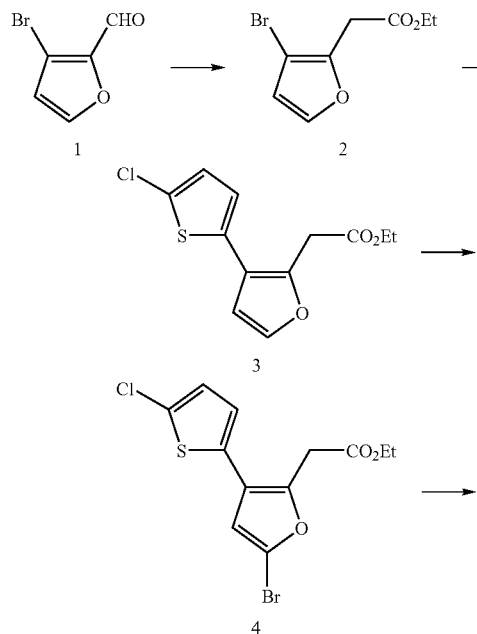

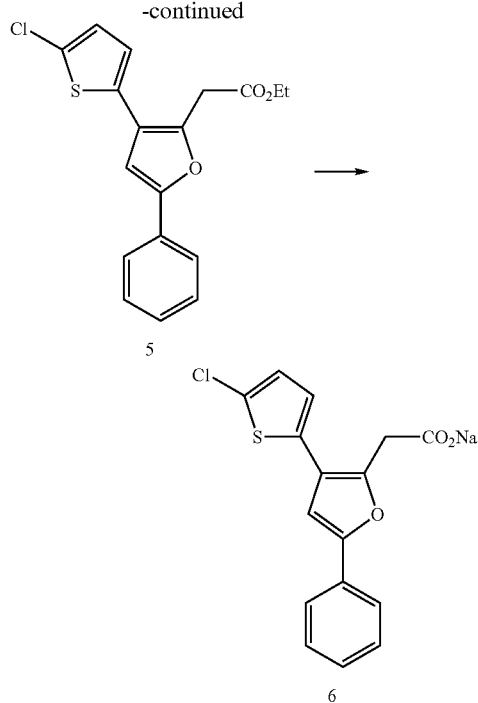

(1) By using compound 1 (875 mg, 5 mmol: Helvetica Chimica Acta, 60, 2085 (1977)), the reaction was carried out in the same manner as in the preparation of compound 3 of Example 1 to give compound 2 (664 mg, 57.0%) as an oily substance. MS•APCI (m/z): 250/252 ([M+NH$_4$]$^+$)

(2) A solution of compound 2 (650 mg, 2.8 mmol), 5-chloro-2-thienyl(tributyl)tin (1.71 g, 4.18 mmol) and PdCl$_2$(PPh$_3$)$_2$ (98 mg, 0.14 mmol) dissolved in toluene (10 ml) was refluxed under heating for 4 hours. To the resulting mixture were added an aqueous potassium fluoride solution (40%, 10 ml) and ethanol (5 ml), and the mixture was stirred for 30 minutes. To the reaction mixture were added water and isopropyl ether, and the resulting mixture was subjected to filtration with Celite. The organic layer of the filtrate was washed with brine, dried over anhydrous sodium sulfate and concentrated under reduced pressure. The residue was purified by silica gel column chromatography (hexane/ethyl acetate=30/1) to give compound 3 (154 mg, 20.4%) as powder.

MS•APCI (m/z): 288/290 ([M+NH$_4$]$^+$)

(3) To a solution of compound 3 (145 mg, 0.54 mmol) in chloroform (5 ml) was added dropwise a bromine (86 mg, 0.54 mmol) solution dissolved in chloroform (1 ml) under ice-cooling. After an hour, an aqueous saturated sodium hydrogen carbonate solution and 15% aqueous sodium thiosulfate solution were added to the reaction mixture, and the resulting mixture was extracted with hexane. The organic layer was washed with brine, dried over anhydrous sodium sulfate and concentrated under reduced pressure. The residue was purified by silica gel column chromatography (hexane/ethyl acetate=50/1) to give compound 4 (47 mg, 25.1%) as an oily substance.

MS•ESI (m/z): 349/351 ([M+H]$^+$)

(4) By using phenyl boric acid (21 mg, 0.17 mmol) and compound 4 (40 mg, 0.11 mmol), the reaction was carried out in the same manner as in the preparation of compound 5 of Example 1 to give compound 5 (32 mg, 80.0%) as an oily substance.

MS•ESI (m/z): 347/349 ([M+H]$^+$)

(5) By using compound 5 (28 mg, 0.08 mmol), the reaction was carried out in the same manner as in the preparation of compound 6 of Example 1 to give a carboxylic acid (20 mg, 77%), and the carboxylic acid (16 mg, 0.05 mmol) was made a sodium salt to give compound 6 (17 mg, 99%).

MS•ESI (m/z): 317/319 ([M−Na]$^+$)

EXAMPLE 3

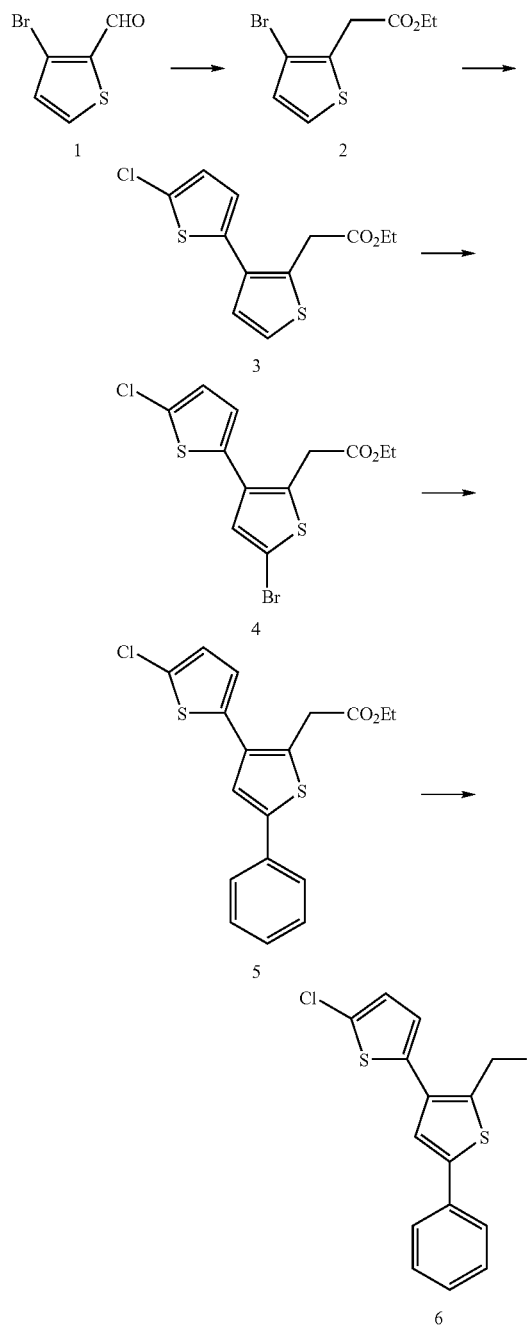

(1) By using compound 1 (5 g, 26.17 mmol), the reaction was carried out in the same manner as in the preparation of compound 1 of Example 2 to give compound 2 (4.58 g, 70.2%) as an oily substance.

MS•APCI (m/z): 266/268 ([M+NH$_4$]$^+$)

(2) By using compound 2 (3.74 g, 15 mmol) and 5-chloro-2-thienyl boric acid (3.17 g, 19.5 mmol), the reaction was carried out in the same manner as in the preparation of compound 5 of Example 2 to give a crude compound 3 (3.35 g) as an oily substance.

MS•APCI (m/z): 304/306 ([M+NH$_4$]$^+$)

(3) By using the crude compound 3 (574 mg, 2.22 mmol) and bromine (384 mg), the reaction was carried out in the same manner as in the preparation of compound 4 of Example 2 to give compound 4 (80 mg, 9% (2 steps)) as an oily substance. MS•APCI (m/z): 382/384 ([M+NH$_4$]$^+$)

(4) By using phenyl boric acid (366 mg, 3 mmol) and compound 4 (731 mg, 2 mmol), the reaction was carried out in the same manner as in the preparation of compound 5 of Example 2 to give compound 5 (552 mg, 72.9%) as an oily substance.

MS•APCI (m/z): 363/365 ([M+H]$^+$)

(5) By using compound 5 (470 mg, 1.24 mmol), the reaction was carried out in the same manner as in the preparation of compound 6 of Example 1 to give compound 6 (91 mg, 20.5%).

MS•ESI (m/z): 333/335 ([M−Na]$^+$)

EXAMPLE 4

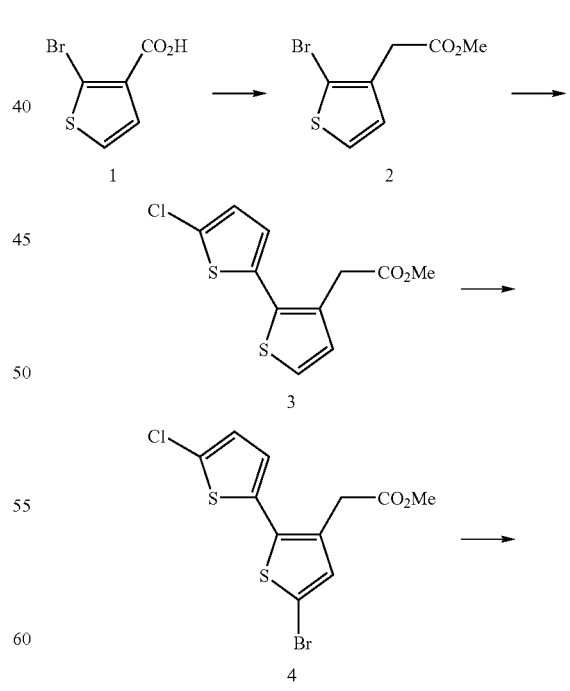

-continued

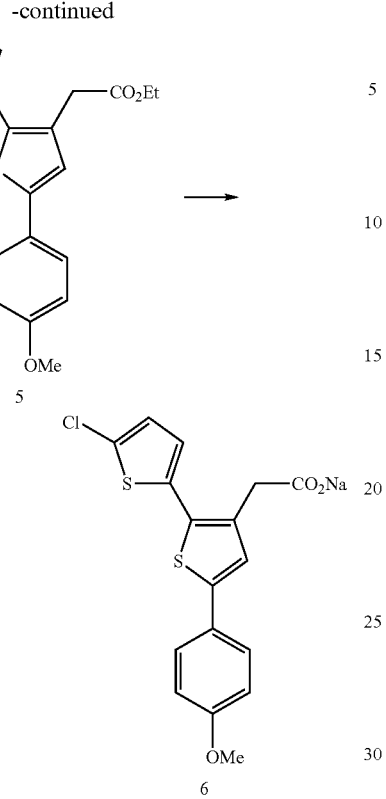

(1) A suspension of compound 1 (25.6 g, 116 mmol: Tetrahedron, 2000, 56, 7205), iodomethane (11.0 ml, 0.177 mmol) and potassium carbonate (24.0 g, 0.174 mmol) was stirred at room temperature overnight. The reaction mixture was poured into water, extracted with ethyl acetate, washed with brine, dried over anhydrous magnesium sulfate and filtered. The filtrate was concentrated and the residue was purified by silica gel column chromatography (hexane/ethyl acetate=20/1) to give compound 2 (23.17 g, 85.1%) as an oily substance.

MS•APCI (m/z): 252/254 ($[M+NH_4]^+$)

(2) By using compound 2 (3.0 g, 12.8 mmol) and 5-chloro-2-thienyl(tributyl)tin (7.80 g, 19.1 mmol), the reaction was carried out in the same manner as in the preparation of compound 3 of Example 2 to give compound 3 (3.09 g, 88.8%) as an oily substance.

MS•APCI (m/z): 273/275 ($[M+H]^+$)

(3) By using compound 3 (3.0 g, 0.011 mmol) and bromine (0.57 ml, 0.011 mmol), the reaction was carried out in the same manner as in the preparation of compound 4 of Example 2 to give compound 4 (3.62 g, 93.6%) as an oily substance.

MS•APCI (m/z): 352/354 ($[M+H]^+$)

(4) By using 4-methoxyphenyl boric acid (325 mg, 2.1 mmol) and compound 4 (500 mg, 1.4 mmol), the reaction was carried out in the same manner as in the preparation of compound 5 of Example 2 to give compound 5 (405 mg, 75.1%) as an oily substance.

MS•APCI (m/z): 379/381 ($[M+H]^+$)

(5) By using compound 5 (345 mg, 0.91 mmol), the reaction was carried out in the same manner as in the preparation of compound 6 of Example 1 to give compound 6 (239 mg).

MS•ESI (m/z): 363/365 ($[M-Na]^+$)

EXAMPLES 5 AND 6

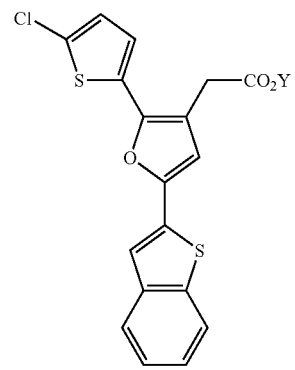

In the same manner as in Example 2, the above-mentioned ethyl ester and carboxylic acid sodium salt were synthesized.

Compound (Y=ethyl) of Example 5: MS•APCI (m/z): 403/405 ($[M+H]^+$)

Compound (Y=Na) of Example 6: MS-ESI (m/z): 373/375 ($[M-Na]^+$)

EXAMPLES 7 and 8

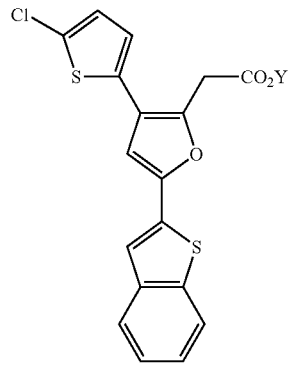

In the same manner as in Example 2, the above-mentioned ethyl ester and carboxylic acid sodium salt were synthesized.

Compound (Y=ethyl) of Example 7: MS•APCI (m/z): 403/405 ($[M+H]^+$)

Compound (Y=Na) of Example 8: MS•ESI (m/z): 329/331 ($[M-Na-CO_2]^+$)

EXAMPLES 9 to 16

In the same manner as in Example 3, compounds of Examples 9 to 16 were synthesized.

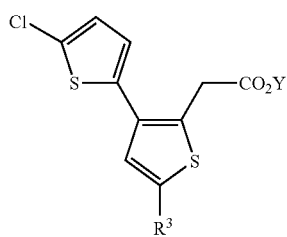

| Example | R³ | Y | MS |
|---|---|---|---|
| 9 | 4-fluorophenyl | ethyl | 381/383 [M + H]⁺ (APCI) |
| 10 | 4-fluorophenyl | Na | 307/309 [M − Na − CO₂]⁻ (ESI) |
| 11 | 2-benzo[b]thienyl | ethyl | 419/421 [M + H]⁺ (APCI) |
| 12 | 2-benzo[b]thienyl | Na | 345/347 [M − Na − CO₂]⁻ (ESI) |
| 13 | 4-methylthiophenyl | ethyl | 409/411 [M + H]⁺ (APCI) |
| 14 | 4-methylthiophenyl | Na | 335/337 [M − Na − CO₂]⁻ (ESI) |
| 15 | 4-methoxyphenyl | ethyl | 393/395 [M + H]⁺ (APCI) |
| 16 | 4-methoxyphenyl | Na | 319/321 [M − Na − CO₂]⁻ (ESI) |

EXAMPLES 17 to 26

In the same manner as in Example 4, compounds of Examples 17 to 26 were synthesized.

| Example | R³ | Y | MS |
|---|---|---|---|
| 17 | 4-fluorophenyl | methyl | 367/369 [M + H]⁺ (APCI) |
| 18 | 4-fluorophenyl | Na | 351/353 [M − Na]⁻ (ESI) |
| 19 | 6-dimethylamino-3-pyridyl | methyl | 393/395 [M + H]⁺ (APCI) |
| 20 | 6-dimethylamino-3-pyridyl | Na | 377/379 [M − Na]⁻ (ESI) |
| 21 | 2-dimethylamino-5-pyrimidinyl | methyl | 394/396 [M + H]⁺ (APCI) |
| 22 | 2-dimethylamino-5-pyrimidinyl | Na | 378/380 [M − Na]⁻ (ESI) |
| 23 | 2-benzo[b]thienyl | methyl | 405/407 [M + H]⁺ (APCI) |
| 24 | 2-benzo[b]thienyl | Na | 389/391 [M − Na]⁻ (ESI) |
| 25 | 4-methylthiophenyl | methyl | 395/397 [M + H]⁺ (APCI) |
| 26 | 4-methylthiophenyl | Na | 379/381 [M − Na]⁻ (ESI) |

EXAMPLE 27

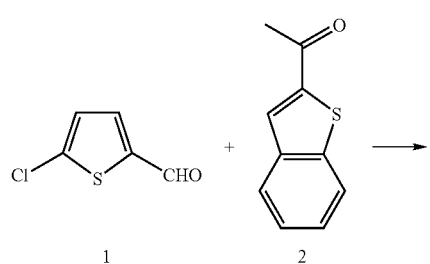

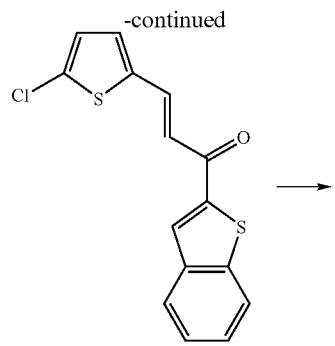

(1) To a solution of compound 1 (1.76 g, 12 mmol) and compound 2 (1.76 g, 10 mmol) dissolved in ethanol (20 ml) was added an aqueous solution of potassium hydroxide (1.12 g, 20 mmol) (1.1 ml). The mixture was stirred at room temperature overnight, and water was added to the mixture and precipitates were collected by filtration. The precipitates were washed with water, dissolved in ethyl acetate-THF, and dried over anhydrous magnesium sulfate. Activated charcoal was added to the extract, and the mixture was filtered and the filtrate was concentrated. The residue was triturated from ethyl acetate-isopropyl ether to give compound 3 (2.36 g, 77%).

MS•APCI (m/z): 305/307 ([M+H]$^+$)

(2) A solution of potassium t-butoxide (22 mg, 0.2 mmol), methyl 3-nitroacrylate (200 mg, 1.5 mmol: A. Rodriguez et al., Tetrahedron Lett., 39, 8563 (1998)) and compound 3 (305 mg, 1 mmol) dissolved in THF (10 ml) was stirred at room temperature overnight. To the reaction mixture was added 10% hydrochloric acid, and the mixture was extracted with ethyl acetate. The organic layer was washed with brine, dried over anhydrous sodium sulfate, and concentrated under reduced pressure. The residue was purified by silica gel column chromatography (chloroform/ethyl acetate=50/1) to give compound 4 (312 mg, 71.2%) as powder. MS•APCI (m/z): 438/440 ([M+H]$^+$)

(3) To a solution of compound 4 (700 mg, 1.6 mmol) and diphenyldisulfide (1.05 g, 4.81 mmol) dissolved in THF was added tri-n-butylphosphine (2.4 ml, 9.64 mmol) at room temperature, and the mixture was refluxed under heating for 2 hours. The reaction mixture was concentrated and purified by silica gel column chromatography (chloroform/hexane=1/1→9/1) to give compound 5 (340 mg, 55%)

MS•APCI (m/z): 388/390 ([M+H]$^+$)

(4) By using compound 5, the reaction was carried out in the same manner as in the preparation of compound 6 of Example 1 to give compound 6.

MS•ESI (m/z): 372/374 ([M-Na]$^+$)

EXAMPLE 28

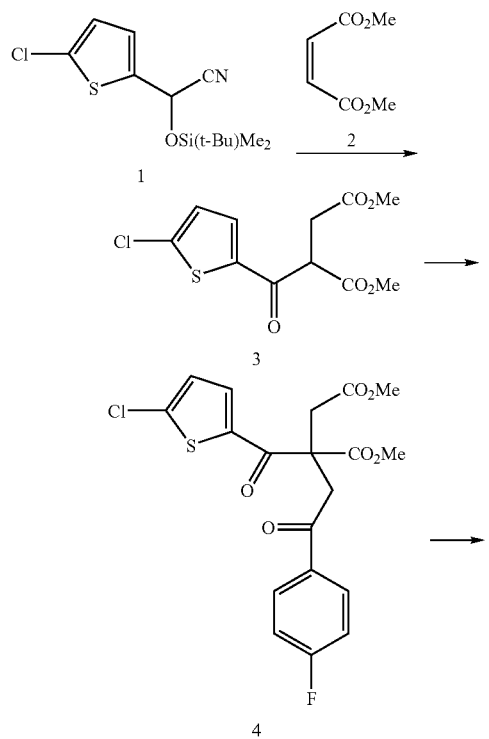

-continued

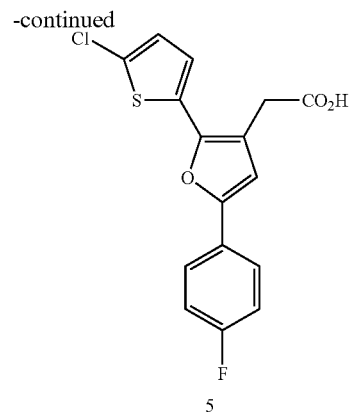

(1) To a solution of diisopropylamine (13.68 g, 135 mmol) dissolved in THF (600 ml) was added n-butyl lithium (1.56 M in Hexane, 85 ml, 135 mmol) under dry ice-acetone cooling, and a solution of compound 1 (38 g, 134 mmol) dissolved in THF (50 ml) was added to the mixture. The resulting mixture was stirred at the same temperature for 25 minutes, and then, a solution of compound 2 (17 ml) dissolved in THF (20 ml) was added to the mixture. The temperature of the reaction mixture was returned to room temperature and the mixture was further stirred for 3.5 hours. After adding a saturated aqueous ammonium chloride solution to the reaction mixture, the resulting mixture was extracted with ethyl acetate. The organic layer was dried over anhydrous sodium sulfate and filtered, and the filtrate was concentrated. The residue was dissolved in THF (750 ml), 1N tetrabutylammonium fluoride (THF solution, 130 ml) was added to the solution and the resulting mixture was stirred for an hour. To the reaction mixture was added an aqueous saturated sodium bicarbonate solution, the resulting mixture was extracted with ethyl acetate, and the extract was dried over anhydrous sodium sulfate. After filtration, the filtrate was concentrated, and the residue was purified by silica gel column chromatography (hexane/ethyl acetate=5/1) to give compound 3 (18.53 g, 48%).

MS•APCI (m/z): 308/310 ([M+NH$_4$]$^+$)

(2) Compound 3 (148 mg, 0.51 mmol) was dissolved in acetone (5 ml), and potassium carbonate (106 mg, 0.77 mmol) and 4-fluorophenacyl bromide (260 mg, 2.4 mmol) were added to the solution and the resulting mixture was stirred overnight. The reaction mixture was concentrated, and then, water was added to the residue and the mixture was extracted with ethyl acetate. The extract was washed with brine, and dried over anhydrous sodium sulfate. After filtration, the filtrate was concentrated, and the residue was purified by silica gel column chromatography to give compound 4 (163 mg, 75%).

MS•APCI (m/z): 427/429 ([M+H]$^+$)

(3) Compound 4 (83.1 mg, 0.195 mmol) was dissolved in acetic acid (2 ml), and conc. hydrochloric acid (0.5 ml) and water (0.5 ml) were added to the solution. The mixture was refluxed under heating for 6 hours, and then, water was added to the mixture and the resulting mixture was extracted with ethyl acetate. The organic layer was washed with brine, and dried over anhydrous sodium sulfate. Activated charcoal was added to the extract and the mixture was filtered, and the filtrate was concentrated to give compound 5 (48 mg, 73%).

MS•ESI (m/z): 335/337 ([M−H]$^-$)

In the same manner as in the above-mentioned Examples, compounds of Examples 29 to 62 were synthesized.

| Example | R³ | Y | Z | MS |
|---|---|---|---|---|
| 29 | 4-fluorophenyl | ethyl | O | 365/367 [M + H]⁺ (APCI) |
| 30 | 4-fluorophenyl | Na | O | 291/293 [M − Na − COO]⁻ (ESI) |
| 31 | 6-dimethylamino-3-pyridyl | ethyl | O | 391/393 [M + H]⁺ (APCI) |
| 32 | 6-dimethylamino-3-pyridyl | Na | O | 317/319 [M − Na − COO]⁻ (ESI) |
| 33 | 6-dimethylamino-3-pyridyl | ethyl | S | 407/409 [M + H]⁺ (APCI) |
| 34 | 6-dimethylamino-3-pyridyl | Na | S | 333/335 [M − Na − COO]⁻ (ESI) |
| 35 | 2-dimethylamino-5-pyrimidinyl | ethyl | O | 392/394 [M + H]⁺ (APCI) |
| 36 | 2-dimethylamino-5-pyrimidinyl | Na | O | 318/320 [M − Na − COO]⁻ (ESI) |
| 37 | 2-dimethylamino-5-pyrimidinyl | ethyl | S | 408/410 [M + H]⁺ (APCI) |
| 38 | 2-dimethylamino-5-pyrimidinyl | Na | S | 334/336 [M − Na − COO]⁻ (ESI) |
| 39 | 4-methylthiophenyl | ethyl | O | 393/395 [M + H]⁺ (APCI) |
| 40 | 4-methylthiophenyl | Na | O | 319/321 [M − Na − COO]⁻ (ESI) |
| 41 | 4-methoxyphenyl | ethyl | O | 377/379 [M + H]⁺ (APCI) |
| 42 | 4-methoxyphenyl | Na | O | 303/305 [M − Na − COO]⁻ (ESI) |

| Example | R¹ | R² | Salt | MS |
|---|---|---|---|---|
| 43 | phenyl | carboxymethyl | Na salt | 249 [M − Na − COO]⁻ (ESI) |
| 44 | 4-chlorophenyl | carboxymethyl | Na salt | 655/657 [2M − 2Na + H]⁻ (ESI) |
| 45 | 3-pyridyl | carboxymethyl | Na salt | 250 [M − Na − COO]⁻ (ESI) |
| 46 | 5-chloro-2-thienyl | 1-carboxy-1-methylethyl | Na salt | 363/365 [M − Na + 2H]⁺ (APCI) |
| 47 | 3-thienyl | carboxymethyl | Na salt | 621 [2M − Na]⁻ (ESI) |
| 48 | 3-pyridyl | Ethyl | hydrochloride | 266 [M + H]⁺ (APCI) |
| 49 | 5-chloro-2-thienyl | carbamoyl-methyl | | 334/336 [M + H]⁺ (APCI) |
| 50 | 5-chloro-2-thienyl | N-methyl-carbamoyl-methyl | | 348/350 [M + H]⁺ (APCI) |
| 51 | 5-chloro-2-thienyl | N,N-dimethyl-carbamoyl-methyl | | 362/364 [M + H]⁺ (APCI) |
| 52 | 5-chloro-2-thienyl | hydroxy-carbamoyl-methyl | | 350/352 [M + H]⁺ (APCI) |
| 53 | 5-chloro-2-thienyl | methoxy-carbamoyl-methyl | | 364/366 [M + H]⁺ (APCI) |

| Example | R³ | Y | MS |
|---|---|---|---|
| 54 | phenyl | ethyl | 347/349 [M + H]⁺ (APCI) |
| 55 | phenyl | Na | 317/319 [M – Na]⁻ (ESI) |
| 56 | 4-fluorophenyl | Na | 335/337 [M – Na]⁻ (ESI) |
| 57 | 6-dimethylamino-3-pyridyl | ethyl | 391/393 [M + H]⁺ (APCI) |
| 58 | 6-dimethylamino-3-pyridyl | Na | 361/363 [M – Na]⁻ (ESI) |
| 59 | 2-dimethylamino-5-pyrimidinyl | ethyl | 392/394 [M + H]⁺ (APCI) |
| 60 | 2-dimethylamino-5-pyrimidinyl | Na | 362/364 [M – Na]⁻ (ESI) |
| 61 | 4-methoxyphenyl | ethyl | 377/379 [M + H]⁺ (APCI) |
| 62 | 4-methoxyphenyl | Na | 347/349 [M – Na]⁻ (ESI) |

EXAMPLE 63

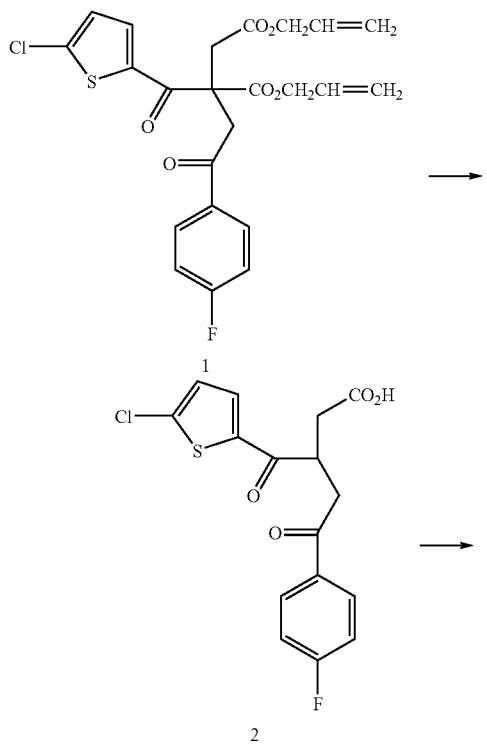

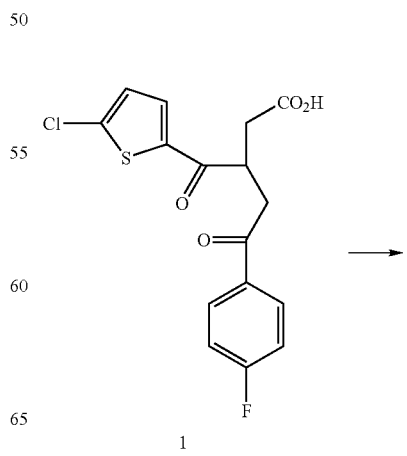

(1) By using compound 1 synthesized in the same manner as in Example 28 except for using diallyl malonate in place of compound 2 in Example 28, to a solution of compound 1 (48 mg, 10 mmol) dissolved in THF (2 ml) were added tetrakis-(triphenylphosphine) palladium (12 mg, 0.01 mmol) and morpholine (0.026 ml), and under argon atmosphere, the mixture was stirred at room temperature overnight. To the reaction mixture was added an aqueous citric acid solution, the resulting mixture was extracted with ethyl acetate, and the organic layer was washed with brine and dried over anhydrous sodium sulfate. After evaporation of the solvent, the residue was purified by silica gel column chromatography (chloroform:methanol=100:0→95:5) to give compound 2 (35 mg, 99%).

MS•ESI (m/z): 353/355 (M–H)

(2) A mixture of compound 2 (209 mg, 0.59 mmol) and ammonium acetate (910 mg, 12 mmol) was stirred at 120° C. for 30 minutes. After cooling the reaction mixture, water was added to the residue and the mixture was extracted with ethyl acetate. The organic layer was washed with brine, dried over anhydrous sodium sulfate, and then, treated with activated charcoal. After evaporation of the solvent, the residue was purified by silica gel column chromatography (chloroform) to give compound 3 (104 mg, 53%).

MS•ESI (m/z): 334/336 (M–H)

Compound 3 was treated with sodium methoxide in the same manner as in Example 1(5) to give a corresponding sodium salt.

MS•ESI (m/z): 334 [M–Na]⁻

EXAMPLE 64

-continued

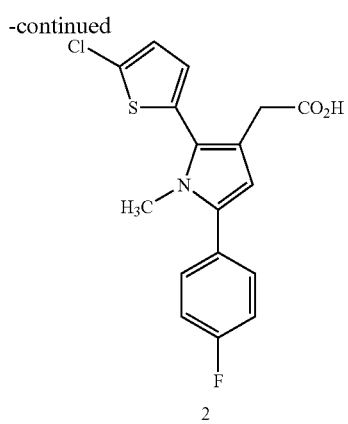

2

In Example 63 (2), by using a solution of methylamine dissolved in methanol in place of ammonium acetate, the same reaction and treatment was carried out to give compound 2.

MS•ESI (m/z): 348/350 (M−H)

Compound 2 was treated with sodium methoxide in the same manner as in Example 1 (5) to give a corresponding sodium salt.

MS•ESI (m/z): 348/350 [M−Na]⁻

In the same manner as in the above-mentioned Examples, compounds of Examples 65 and 66 were synthesized.

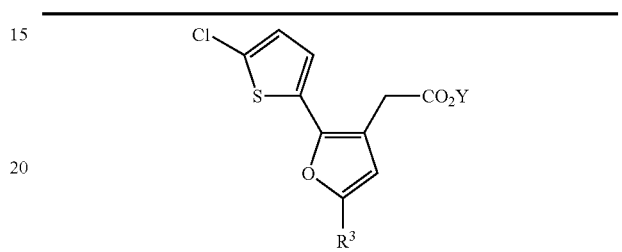

| Example | R³ | Y | R⁴ | MS |
|---|---|---|---|---|
| 65 | phenyl | Na | H | 316/318 [M − Na]⁻ (ESI) |
| 66 | 2-benzo[b]thienyl | Na | H | 372/374 [M − Na]⁻ (ESI) |

REFERENCE EXAMPLE 1

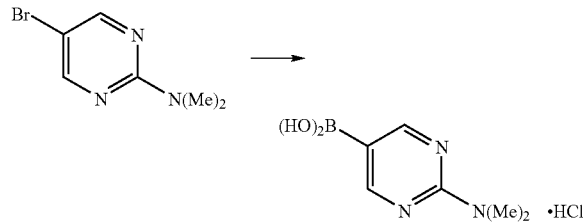

To a solution of 5-bromo-2-dimethylaminopyrimidine (2.0 g, 9.9 mmol: Bull. Chem. Soc. Jpn., 72, 2523 (1999)) dissolved in THF (25 ml) was added 1.56 M of n-butyl lithium (hexane solution, 7.0 ml, 10.9 mmol) under cooling with a dry ice-acetone bath. After stirring the mixture for 40 minutes, a solution of triisopropyl borate (3.5 ml, 0.15 ml) dissolved in THF (6 ml) was added to the reaction mixture. The temperature of the mixture was raised to room temperature, hydrochloric acid was added to the mixture, and then the solvent was removed. The residue was triturated by methanol-diethyl ether to give 2-dimethylamino-5-pyrimidinylboric acid hydrochloride (2.26 g).

The compound obtained in Reference example 1 was used in the preparation of compound of Examples 21 and 22.

In the same manner as in the above-mentioned Examples and Reference examples, compound mentioned below can be further synthesized.

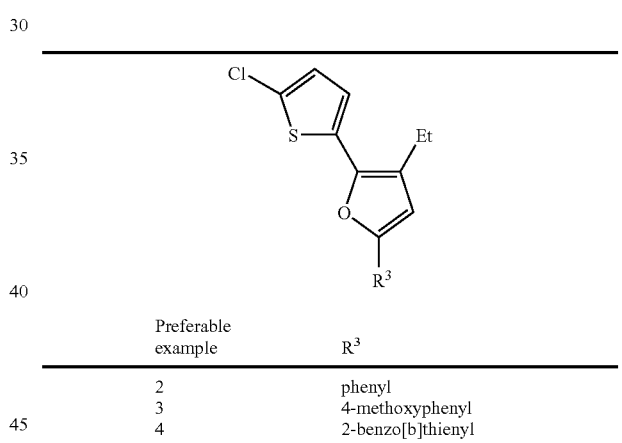

| Preferable example | R³ | Y |
|---|---|---|
| 1 | 4-fluorophenyl | ethyl |

| Preferable example | R³ |
|---|---|
| 2 | phenyl |
| 3 | 4-methoxyphenyl |
| 4 | 2-benzo[b]thienyl |

| Preferable example | R³ | Y | R⁴ |
|---|---|---|---|
| 5 | phenyl | ethyl | H |
| 6 | phenyl | Na | H |
| 7 | phenyl | Na | methyl |
| 8 | phenyl | Na | methyl |
| 9 | 4-fluorophenyl | ethyl | H |
| 10 | 4-fluorophenyl | Na | H |

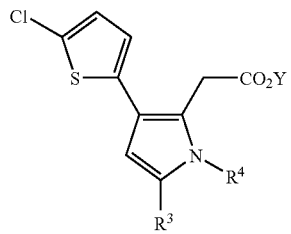

| Preferable example | R³ | Y | R⁴ |
|---|---|---|---|
| 11 | 6-dimethylamino-3-pyridyl | ethyl | H |
| 12 | 6-dimethylamino-3-pyridyl | Na | H |
| 13 | 2-dimethylamino-5-pyrimidinyl | ethyl | H |
| 14 | 2-dimethylamino-5-pyrimidinyl | Na | H |
| 15 | 2-benzo[b]thienyl | ethyl | H |
| 16 | 4-methylthiophenyl | ethyl | H |
| 17 | 4-methylthiophenyl | Na | H |
| 18 | 4-methoxyphenyl | ethyl | H |
| 19 | 4-methoxyphenyl | Na | H |

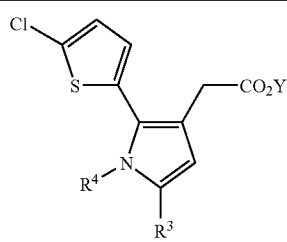

| Preferable example | R³ | Y | R⁴ |
|---|---|---|---|
| 20 | phenyl | ethyl | H |
| 21 | phenyl | Na | methyl |
| 22 | 4-fluorophenyl | ethyl | H |
| 23 | 6-dimethylamino-3-pyridyl | ethyl | H |
| 24 | 6-dimethylamino-3-pyridyl | Na | H |
| 25 | 2-dimethylamino-5-pyrimidinyl | ethyl | H |
| 26 | 2-dimethylamino-5-pyrimidinyl | Na | H |
| 27 | 2-benzo[b]thienyl | ethyl | H |
| 28 | 4-methylthiophenyl | ethyl | H |
| 29 | 4-methylthiophenyl | Na | H |
| 30 | 4-methoxyphenyl | ethyl | H |
| 31 | 4-methoxyphenyl | Na | H |

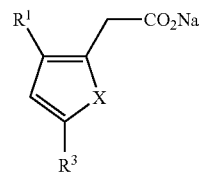

| Preferable example | X | R¹ | R³ |
|---|---|---|---|
| 32 | O | 3,4-difluorophenyl | phenyl |
| 33 | S | 3,4-difluorophenyl | phenyl |
| 34 | O | 3,4-difluorophenyl | 2-dimethylamino-pyrimidin-5-yl |
| 35 | S | 3,4-difluorophenyl | 2-dimethylamino-pyrimidin-5-yl |
| 36 | O | 3,4-difluorophenyl | 4-methoxyphenyl |
| 37 | S | 3,4-difluorophenyl | 4-methoxyphenyl |
| 38 | O | 4-chloro-3-fluorophenyl | phenyl |
| 39 | S | 4-chloro-3-fluorophenyl | phenyl |
| 40 | O | 4-chloro-3-fluorophenyl | 2-dimethylamino-pyrimidin-5-yl |
| 41 | S | 4-chloro-3-fluorophenyl | 2-dimethylamino-pyrimidin-5-yl |
| 42 | O | 4-chloro-3-fluorophenyl | 4-methoxyphenyl |
| 43 | S | 4-chloro-3-fluorophenyl | 4-methoxyphenyl |

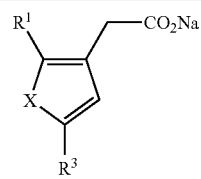

| Preferable example | X | R¹ | R³ |
|---|---|---|---|
| 44 | O | 3,4-difluorophenyl | 4-fluorophenyl |
| 45 | S | 3,4-difluorophenyl | 4-fluorophenyl |
| 46 | O | 3,4-difluorophenyl | 2-dimethylamino-pyridin-5-yl |
| 47 | S | 3,4-difluorophenyl | 2-dimethylamino-pyridin-5-yl |
| 48 | O | 3,4-difluorophenyl | 4-methoxyphenyl |
| 49 | S | 3,4-difluorophenyl | 4-methoxyphenyl |
| 50 | O | 4-chloro-3-fluorophenyl | 4-fluorophenyl |
| 51 | S | 4-chloro-3-fluorophenyl | 4-fluorophenyl |
| 52 | O | 4-chloro-3-fluorophenyl | 2-dimethylamino-pyridin-5-yl |
| 53 | S | 4-chloro-3-fluorophenyl | 2-dimethylamino-pyridin-5-yl |
| 54 | O | 4-chloro-3-fluorophenyl | 4-methoxyphenyl |
| 55 | S | 4-chloro-3-fluorophenyl | 4-methoxyphenyl |

EXPERIMENTAL EXAMPLE 1

Relaxation Effect on Potassium-Induced Contraction of Isolated Rabbit Urinary Bladder Urinary bladder was isolated from Male NZW rabbits (body weight: 2.0-3.5 kg) and immersed in ice-cold Krebs-bicarbonate solution (in mM: 118 NaCl, 4.7 KCl, 2.55 $CaCl_2$, 1.18 MgSO$_4$, 1.18 KH$_2$PO$_4$, 24.88 NaHCO$_3$ and 11.1 glucose). The urinary bladder was cut into longitudinal strips (5 mm length 3-4 mm width) after mucosal layer was removed.

Preparations were mounted in organ baths containing 10 ml of Krebs solution maintained at 37° C. and gassed with 95% O$_2$/5% CO$_2$. Accordingly, preparations were stretched with an initial tension of 2.0±1.0 g, and changes in isometric tension were measured by force-displacement transducer. The preparations were pre-contracted by changing organ-bath solution into high-K$^+$ (30 mM) Krebs solution (in mM: 118 NaCl, 4.7 KCl, 2.55 CaCl$_2$, 1.18 MgSO$_4$, 1.18 KH$_2$PO$_4$, 24.88 NaHCO$_3$ and 11.1 glucose).

After stable tension was obtained, compounds were added into organ baths cumulatively (10$^{-8}$ M-10$^{-4}$ M). The effects of compounds were expressed as a percentage of the maximum relaxation produced by 10$^{-4}$ M papaverine as 100%. 50% relaxation concentration (IC$_{50}$) was calculated and IC$_{50}$ value range (μM) of compounds of the present invention was shown in the following Table 1 with a rank of A, B or C. These ranges are as mentioned below.

3 μM≧C>1 μM≧B>0.5 μM≧A

TABLE 1

| Example | IC$_{50}$ value |
| --- | --- |
| 2 (Compound 6) | A |
| 3 (Compound 6) | B |
| 6 | A |
| 8 | A |
| 10 | A |
| 14 | B |
| 16 | C |
| 26 | A |

EXPERIMENTAL EXAMPLE 2

Inhibitory Effect on the Rhythmic Bladder Contractions Induced by Substance P in Anesthetized Rats For the experiments, Sprague-Dawley female rats (9 to 12 weeks old) weighing between 200 to 300 g were used. After urethane anesthetization (subcutaneously administered with a dose of 1.2 g/kg), cannulae were placed in both right and left femoral veins. One intravenous catheter was used for administration of compounds, and the other was for the substance P (0.33 μg/kg/min) infusion. We also cannulated into ureter to pass urine. Polyethylene catheters were inserted into carotid artery for continuous monitoring of arterial blood pressure and heart rate. For continuous infusion, transurethral bladder catheter was inserted into the bladder through the urethra and tied in place by a ligature around the urethral orifice. One end of the catheter was attached to a pressure transducer in order to measure intravesical pressure. The other end of the catheter was used for infusion of saline into the bladder. After stabilization of blood pressure and heart rate and after the bladder was emptied, cystometry was performed by filling the bladder slowly with about 0.6 ml of saline. After about 10 minutes, intravenous infusion of substance P (0.33 μg/kg/min) was started for stabilization of the micturition reflex. Compounds were administered after stable rhythmic bladder contraction was obtained over 15 minutes. All compounds were dissolved or suspended in saline containing 0.5% Tween 80 for intravenous administration (0.1 ml/kg). The rhythmic contraction frequency and the intravesical pressure were observed for 35 minutes after administration of the test compound.

As a result, compounds of the present invention decreased the frequency of bladder rhythmic contraction without changing the amplitude of contraction. Also, we determined a time (minute) during which the frequency of the rhythmic contraction had been completely inhibited by administering 0.25 mg/kg of compound. A 100% inhibition time (minute) of the selected compounds of the present invention is shown in the following Table 2.

TABLE 2

| Example | 100% inhibiting time (min) |
| --- | --- |
| 2 (Compound 6) | 13.1 |
| 3 (Compound 6) | 27.1 |
| 6 | 16.8 |
| 18 | 12.5 |
| 36 | 15.3 |
| 58 | 23.8 |

Active ingredients of the present invention showed relaxation effect on 20 mM K$^+$-contracted preparation and the effect was blocked by iberiotoxin, a selective large conductance calcium-activated K channel blocker.

Also in in vivo animal study, pre-administration of iberiotoxin (0.15 mg/kg, intravenous administration) reduced inhibitory effect of active ingredients in the present invention on the rhythmic bladder contraction. Thus, it is suggested from the results that the active ingredients of the present invention have a detrusor relaxing activity through the large conductance calcium-activated K channel.

Thus, it was shown that compounds which are active ingredients of the present invention were effective for prophylaxis and treatment of diseases such as pollakiuria, urinary incontinence and the like through the large conductance calcium-activated K channel opening activity.

INDUSTRIAL APPLICABILITY

The 5-membered heterocyclic compound (I) or a pharmaceutically acceptable salt which is an active ingredient of the present invention has an excellent large conductance calcium-activated K channel opening activity and hyperpolarizes a membrane electric potential of cells, so that it is useful for a prophylactic, relief and/or treatment agent of, for example, hypertension, premature birth, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, male-pattern baldness, erectile dysfunction, diabetes, diabetic peripheral nerve disorder, other diabetic complication, sterility, urolithiasis and pain accompanied thereby, pollakiuria, urinary incontinence, nocturnal enuresis, asthma, chronic obstructive pulmonary disease (COPD), cough accompanied by asthma or chronic obstructive pulmonary disease (COPD), cerebral apoplexy, cerebral ischemia, traumatic encephalopathy, and the like.

Also, the 5-membered heterocyclic compound (I) or a pharmaceutically acceptable salt has a low toxicity, so that it has high safety as a medicine.

The invention claimed is:

1. A method for treatment of irritable bowel syndrome, chronic heart failure, angina, cardiac infarction, cerebral infarction, pollakiuria, urinary incontinence, or, cerebral ischemia, which comprises administering an effective amount of a 5-membered heterocyclic compound of the formula (I):

wherein ring A is a ring represented by one of the formulae:

R¹ is a substituted or unsubstituted thiophene;
R² is an alkyl substituted by carboxy; and
R³ is a substituted or unsubstituted pyridyl, a substituted or unsubstituted pyrimidinyl;
or a pharmaceutically acceptable salt thereof as an active ingredient.

2. The method according to claim 1,
wherein R¹ is thiophene which may be substituted by a substituent(s) selected from the group consisting of nitro, hydroxy, formyl, carbamoyl, cyano, amino, carboxy, alkoxycarbonyl, halogen, alkyl, hydroxyalkyl, alkoxy, mono- or di-alkylamino, mono- or di-alkanoylamino, alkylthio, alkylsulfonyl, alkylsulfinyl, sulfamoyl and mono- or di-alkylsulfamoyl
R³ is (1) a pyridine which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (2) a pyrimidine which may be substituted by a substituent(s) selected from the group consisting of oxo, cyano, nitro, amino, halogen, carboxy, hydroxy, formyl, carbamoyl, mono- or di-alkylamino, N-alkyl-N-cycloalkylamino, aminoalkyl, mono- or di-alkylaminoalkyl, mono- or di-alkylcarbamoyl, alkyl, hydroxyalkyl, alkoxy, alkoxyalkyl, alkoxycarbonyl, alkanoyl, sulfo, alkylthio, alkylsulfonyl, sulfamoyl, mono- or di-alkylsulfamoyl, alkylsulfinyl and heterocycle or (3) an alkyl which may be substituted by a substituent(s) selected from the group consisting of hydroxy, cyano, carboxy, carbamoyl, amino, mono- or di-alkylamino, alkanoylamino, alkylsulfonylamino, hydroxyamino, mono- or di-alkylcarbamoyl, trifluoromethyl, halogen, alkoxy, alkylthio, alkylsulfinyl, alkylsulfonyl, sulfamoyl, mono- or di-alkylsulfamoyl, alkoxycarbonyl and heterocycle.

3. The method according to claim 1,
wherein R¹ is a thiophene which may be substituted by halogen or alkyl; and
R³ is (1) a pyridyl which may be substituted by one or two substituent(s) selected from the group consisting of amino, halogen, alkyl, alkoxy, mono- or di-alkylamino and alkylthio or (2) pyrimidinyl which may be substituted by one or two substituent(s) selected from the group consisting of amino, halogen, alkyl, alkoxy, mono- or di-alkylamino and alkylthio.

4. The method according to claim 1, wherein R¹ is (1) thienyl which may be substituted by halogen; and R³ is (1) pyridyl which may be substituted by a substituent(s) selected from the group consisting of alkyl, alkoxy and dialkylamino, or (2) pyrimidinyl which may be substituted by alkoxy, alkyl, dialkylamino or alkylthio.

5. The method according to claim 1,
wherein R¹ is (1) thienyl which may be substituted by halogen;
R³ is (1) pyridyl which may be substituted by a substituent(s) selected from the group consisting of alkyl, alkoxy and dialkylamino, or (2) pyrimidinyl which may be substituted by alkoxy or dialkylamino.

6. The method according to claim 1,
wherein R¹ is thienyl which may be substituted by halogen; and
R³ is (1) pyridyl which may be substituted by alkoxy or dialkylamino, or (2) pyrimidinyl which may be substituted by dialkylamino.

7. The method according to claim 1, wherein R² is carboxymethyl.

8. The method according to claim 1, wherein the Ring A is a ring represented by the following formula:

9. The method according to claim 1, which is for the treatment of pollakiuria or urinary incontinence.

* * * * *